US008895028B2

(12) United States Patent
Smith et al.

(10) Patent No.: US 8,895,028 B2

(45) Date of Patent: Nov. 25, 2014

(54) METHODS AND COMPOSITIONS FOR DENGUE VIRUS 3 (DV3) INFECTIOUS CLONE

(71) Applicant: Arbovax, Inc., Raleigh, NC (US)

(72) Inventors: Katherine M. Smith, Raleigh, NC (US); Raquel Hernandez, Raleigh, NC (US)

(73) Assignee: Arbovax, Inc., Raleigh, NC (US)

( * ) Notice: Subject to any disclaimer, the term of this patent is extended or adjusted under 35 U.S.C. 154(b) by 0 days.

(21) Appl. No.: 13/789,281

(22) Filed: Mar. 7, 2013

(65) Prior Publication Data

US 2014/0024081 A1 Jan. 23, 2014

Related U.S. Application Data

(60) Provisional application No. 61/674,137, filed on Jul. 20, 2012.

(51) Int. Cl.

| | |
|---|---|
| ***A61K 35/76*** | (2006.01) |
| ***C12N 15/40*** | (2006.01) |
| ***C07K 14/08*** | (2006.01) |
| ***C07K 14/18*** | (2006.01) |
| ***C12N 7/00*** | (2006.01) |

(52) U.S. Cl.

CPC . *A61K 35/76* (2013.01); *C12N 7/00* (2013.01); *C12N 2700/00* (2013.01)

USPC .................... 424/218.1; 424/93.1; 424/184.1; 536/23.1; 435/320.1; 435/235.1; 435/325

(58) Field of Classification Search

CPC ............ A61K 39/12; A61K 2039/525; A61K 31/7088; C12N 2770/00; C12N 2770/24011

See application file for complete search history.

(56) References Cited

U.S. PATENT DOCUMENTS

| | | | | |
|---|---|---|---|---|
| 6,306,401 | B1 * | 10/2001 | Brown et al. | 424/218.1 |
| 6,589,533 | B1 * | 7/2003 | Brown et al. | 424/205.1 |
| 6,593,111 | B2 | 7/2003 | Baric et al. | |
| 7,226,602 | B2 | 6/2007 | Whitehead et al. | |
| 7,335,363 | B2 * | 2/2008 | Hernandez et al. | 424/199.1 |
| 7,517,531 | B2 | 4/2009 | Whitehead et al. | |
| 7,560,118 | B2 | 7/2009 | Whitehead et al. | |
| 8,075,903 | B2 | 12/2011 | Whitehead et al. | |
| 2004/0259224 | A1 | 12/2004 | Guirakhoo | |
| 2008/0107685 | A1 | 5/2008 | Barban et al. | |
| 2009/0004721 | A1 | 1/2009 | Keelapang et al. | |
| 2009/0258036 | A1 | 10/2009 | Whitehead et al. | |
| 2010/0104598 | A1 | 4/2010 | Whitehead et al. | |
| 2010/0158938 | A1 | 6/2010 | Guirakhoo | |
| 2010/0255030 | A1 * | 10/2010 | Kinney et al. | 424/202.1 |
| 2010/0270202 | A1 * | 10/2010 | Guy et al. | 206/570 |
| 2010/0278773 | A1 * | 11/2010 | Chambers et al. | 424/85.2 |
| 2010/0291144 | A1 * | 11/2010 | Ramanathan et al. | 424/208.1 |
| 2011/0236421 | A1 * | 9/2011 | Brown et al. | 424/218.1 |
| 2013/0202634 | A1 * | 8/2013 | Shresta et al. | 424/186.1 |
| 2013/0216575 | A1 * | 8/2013 | Coller et al. | 424/218.1 |
| 2013/0243812 | A1 * | 9/2013 | Pugachev | 424/199.1 |
| 2013/0323278 | A1 * | 12/2013 | Chambers | 424/205.1 |
| 2014/0024081 | A1 * | 1/2014 | Smith et al. | 435/91.3 |

FOREIGN PATENT DOCUMENTS

WO WO 03/092592 A2 11/2003

OTHER PUBLICATIONS

Smith KM, Nanda K, Spears CJ, Ribeiro M, Vancini R, Piper A, Thomas GS, Thomas ME, Brown DT, Hernandez R. Structural mutants of dengue virus 2 transmembrane domains exhibit host-range phenotype. Virol J. Jun. 9, 2011;8:289.*

Smith KM, Nanda K, Spears CJ, Piper A, Ribeiro M, Quiles M, Briggs CM, Thomas GS, Thomas ME, Brown DT, Hernandez R, McCarl V. Testing of novel dengue virus 2 vaccines in African green monkeys: safety, immunogenicity, and efficacy. Am J Trop Med Hyg. Oct. 2012;87(4):743-53. Epub Aug. 13, 2012.*

Ramírez A, Fajardo A, Moros Z, Gerder M, Caraballo G, Camacho D, Comach G, Alarcón V, Zambrano J, Hérnandez R, Moratorio G, Cristina J, Liprandi F. Evolution of dengue virus type 3 genotype III in Venezuela: diversification, rates and population dynamics. Virol J. Nov. 18, 2010;7:329.*

Richards SL, Anderson SL, Alto BW. Vector competence of *Aedes aegypti* and *Aedes albopictus* (*Diptera: Culicidae*) for dengue virus in the Florida Keys. J Med Entomol. Jul. 2012;49(4):942-6.*

Beckett CG, Tjaden J, Burgess T, Danko JR, Tamminga C, Simmons M, Wu SJ, Sun P, Kochel T, Raviprakash K, Hayes CG, Porter KR. Evaluation of a prototype dengue-1 DNA vaccine in a Phase 1 clinical trial. Vaccine. Jan. 29, 2011;29(5):960-8. doi: 10.1016/j.vaccine.2010.11.050. Epub Nov. 25, 2010.*

Capeding RZ, Luna IA, Bomasang E, Lupisan S, Lang J, Forrat R, Wartel A, Crevat D. Live-attenuated, tetravalent dengue vaccine in children, adolescents and adults in a dengue endemic country: randomized controlled phase I trial in the Philippines. Vaccine. May 17, 2011;29(22):3863-72. Epub Apr. 6, 2011.*

Raviprakash K, Luke T, Doukas J, Danko J, Porter K, Burgess T, Kochel T. A dengue DNA vaccine formulated with Vaxfectin® is well tolerated, and elicits strong neutralizing antibody responses to all four dengue serotypes in New Zealand white rabbits. Hum Vaccin Immunother. Dec. 1, 2012;8(12):1764-8. Epub Oct. 2, 2012.*

"Arbovax Raises $1.7M with Help from Piedmont Angels, Mario Partners, Guardant Partners"—cbl—May 26, 2011. http://charlotteraleigh.citybizlist.com/article/arbovax-raises-17m-help-piedmont-angels-mario-partners-guardant-partners-cbl-0.*

(Continued)

*Primary Examiner* — Benjamin P Blumel
*Assistant Examiner* — Rachel Gill
(74) *Attorney, Agent, or Firm* — Myers Bigel Sibley & Sajovec, PA

(57) ABSTRACT

The present invention provides a nucleic acid molecule comprising a nucleotide sequence encoding an infectious RNA molecule encoding a live viral strain of a dengue 3 virus (DV3), wherein said nucleotide sequence is the nucleotide sequence of SEQ ID NO:1 or a nucleotide sequence having at least 99% identity with the nucleotide sequence of SEQ ID NO.1.

7 Claims, 3 Drawing Sheets

(56) References Cited

OTHER PUBLICATIONS

Attatippaholkun WH, et. al. Dengue virus 3 strain CH53498, complete genome, GenBank Acc. No. DQ863638, Dep. Oct. 14, 2009.*
Henn MR, et. al. Dengue virus 3 isolate DENV-3/TH/BID-V3360/1973, complete genome, GenBank Acc. No. GQ868593, Dep. Sep. 30, 2009.*
Sriburi R, Keelapang P, Duangchinda T, Pruksakorn S, Maneekarn N, Malasit P, Sittisombut N. Construction of infectious dengue 2 virus cDNA clones using high copy number plasmid. J Virol Methods. Mar. 2001;92(1):71-82.*
Henn et. al. Dengue virus 3 isolate DENV-3/TH/BID-V3360/1973, complete genome, NCBI GenBank Dep. No. GQ868593, Deposited Sep. 30, 2009.*
Blaney et al. "Genetically modified live attenuated dengue virus type 3 vaccine candidates" *Am. J. Trop. Med. Hyg.* 71(6):811-821 (2004).
GenBank Accession No. DQ863638 "Dengue virus 3 strain CH53489, complete genome" Oct. 14, 2009 (5 pages).
GenBank Accession No. JQ411814 "Dengue virus 3 isolate UNC2001, complete genome" Apr. 30, 2012 (5 pages).
Messer et al. "Development and characterization of a reverse genetic system for studying dengue virus serotype 3 strain variation and neutralization" *PLOS Negl Trop Dis* 6(2):e1486, 2012.

* cited by examiner

METHODS AND COMPOSITIONS FOR DENGUE VIRUS 3 (DV3) INFECTIOUS CLONE

STATEMENT OF PRIORITY

This application claims the benefit, under 35 U.S.C. §119(e), of U.S. Provisional Patent Application Ser. No. 61/674,137, filed Jul. 20, 2012, the entire contents of which are incorporated by reference herein.

STATEMENT REGARDING ELECTRONIC FILING OF A SEQUENCE LISTING

A Sequence Listing in ASCII text format, submitted under 37 C.F.R. §1.821, entitled 9856-3_ST25.txt, 49,673 bytes in size, generated on Mar. 7, 2013 and filed via EFS-Web, is provided in lieu of a paper copy. This Sequence Listing is hereby incorporated by reference into the specification for its disclosures.

FIELD OF THE INVENTION

The present invention relates to an infectious clone of a dengue 3 virus (DV3) for use in therapeutic, vaccine and diagnostic applications.

BACKGROUND OF THE INVENTION

Dengue viruses (DVs) are positive sense, single-stranded RNA viruses belonging to the *Flavivirus* genus of the Flaviviridae family. The genomic organization consists of the following elements: 5' noncoding region (NCR), structural proteins (capsid (C), premembrane/membrane (prM/M), envelope (E)) and nonstructural proteins (NS1-NS2A-NS2B-N53-NS4A-NS4B-NS5), and 3' NCR. Similar to other flaviviruses, the DV viral genome encodes an uninterrupted coding region which is translated into a single polyprotein. The genomic RNA contains a type I cap at the 5' end but lacks a poly-A tail at the 3' end.

The viruses are maintained in a cycle which involves humans and *Aedes aegypti* as well as *Aedes albopictus* mosquitoes. The infection in humans is initiated by injection of the virus while an infected mosquito takes a blood meal. The virus in the mosquito's saliva is deposited mainly in the extravascular tissues. The first category of cells infected after inoculation are dendritic cells, which then migrate to the lymph nodes (Wu et al. *Nature Med.* 7:816-820 (2000)). After an initial replication in the skin and in the lymph nodes, the virus appears in the blood during the acute febrile phase, generally for 3 to 5 days.

Dengue diseases are caused by four virus serotypes (DV1, DV2, DV3, and DV4) of the Flavivirus genus. Infection with a dengue serotype can produce a clinical disease spectrum ranging from a nonspecific viral syndrome to a severe hemorrhagic disease which can be fatal. The incubation period of dengue fever after a mosquito bite is approximately 4 days (ranging from 3 to 14 days). Dengue fever is characterized by a biphasic fever, headaches, pain in various parts of the body, prostration, eruptions, lymphadenopathy and leukopenia (Kautner et al. J. of *Pediatrics* 131:516-524 (1997); Rigau-Perez et al. *Lancet;* 352: 971-977 (1998)). The viremia period is the same as for febrile diseases (Vaughn et al. *J. Infect. Dis.* 176:322-30 (1997)). Recovery from dengue fever occurs after 7 to 10 days, but there is usually a prolonged asthenia. Decreases in leukocyte and platelet count are common.

Hemorrhagic dengue is a severe febrile disease characterized by anomalies in homeostasis and an increase in vascular permeability that can result in hypovolemia and in hypotension (dengue with shock syndrome) often complicated by severe internal hemorrhaging. The mortality rate of hemorrhagic dengue can be up to 10% without treatment, but is 1% in most centers with experience in treatment (WHO Technical Guide, 1986. "Dengue haemorrhagic fever: diagnosis, treatment and control" pp. 1-2. World Health Organization, Geneva, Switzerland).

Dengue is the second most common tropical infectious disease after malaria and more than half the world's population (2.5 billion) lives in regions where there is a risk of epidemic transmission. Each year, cases of dengue are estimated at 50-100 million, cases of patients hospitalized for hemorrhagic dengue at 500 000, and the number of deaths at 25 000. Dengue is endemic in Asia, in the Pacific region, in Africa, in Latin America and in the Caribbean. More than 100 tropical countries are endemic for dengue virus infections and hemorrhagic dengue has been documented in 60 of these countries (Gubler, *TRENDS in Microbiology* 10:100-103 (2002); Monath. *Proc. Natl. Acad. Sci. USA* 91:2395-2400 (1994)).

There is no specific therapeutic for diseases caused by infection by dengue virus. The treatment for dengue fever is symptomatic, with confinement to bed, control of fever and pain with antipyretics and analgesics, and adequate fluid intake. The treatment for hemorrhagic dengue requires equilibration of fluid losses, replacement of clotting factors and heparin infusion.

Preventive measures are currently based on controlling the vector and taking personal protection steps which are difficult to implement and expensive. No vaccine against dengue has been approved at this time. Given that the four dengue serotypes are in circulation in the world and since they have been reported as being involved in cases of dengue hemorrhagic fever, immunization should ideally confer protection against the four serotypes of the dengue virus.

Recombinant DNA technology has made it possible to develop live attenuated dengue virus vaccine candidates. Methods have been developed to recover infectious dengue virus from cells transfected with RNA transcripts derived from a full-length cDNA clone of the dengue virus genome, thus making it possible to derive infectious viruses into which attenuating mutations can be introduced (e.g., via the cDNA clone by site-directed mutagenesis).

Thus, the present invention provides methods and compositions for a DV3 infectious clone for use in therapeutic, vaccine and diagnostic applications.

SUMMARY OF THE INVENTION

In one aspect, the present invention provides an isolated nucleic acid molecule comprising a nucleotide sequence encoding an infectious RNA molecule encoding a live viral strain of a dengue 3 virus (DV3), wherein said nucleotide sequence is the nucleotide sequence of SEQ ID NO:1 or a nucleotide sequence having at least 99% identity with the nucleotide sequence of SEQ ID NO:1.

In a further aspect, the present invention provides an isolated infectious RNA molecule encoded by the nucleic acid molecule of this invention, wherein the infectious RNA molecule encodes a live viral strain of dengue 3 virus. In some embodiments, the RNA molecule comprises, consists essentially of or consists of the nucleotide sequence of SEQ ID NO:3.

Also provided herein is a method of producing a nucleic acid molecule comprising a nucleotide sequence encoding an infectious RNA molecule encoding a live viral strain of a dengue 3 virus (DV3), wherein said nucleotide sequence is the nucleotide sequence of SEQ ID NO:1 or a nucleotide sequence having at least 99% identity with the nucleotide sequence of SEQ ID NO:1, comprising: a) producing Clone 1 (ABV-DEN3ME) and amplifying Clone 1 in *E. coli* cells in culture; b) producing Clone 2 (ABV-DEN3ΔME) and amplifying Clone 2 in *E. coli* cells in culture; c) isolating the amplified Clone 1 and Clone 2 from the cells of (a) and (b), respectively; d) digesting the isolated Clone 1 of (c) with Cla I restriction enzyme to cut out a segment consisting of preM, E, and first 120 bp of NS1; e) digesting the isolated Clone 2 of (c) with Cla I restriction enzyme to linearize Clone 2; and f) ligating the linearized Clone 2 of (e) with the segment of (d) to produce the nucleic acid molecule. The present invention further provides an isolated nucleic acid molecule produced by this method.

Additional aspects of the present invention include a method of producing an infectious RNA molecule encoded by a nucleic acid molecule comprising a nucleotide sequence encoding an infectious RNA molecule encoding a live viral strain of a dengue 3 virus (DV3), wherein said nucleotide sequence is the nucleotide sequence of SEQ ID NO:1 or a nucleotide sequence having at least 99% identity with the nucleotide sequence of SEQ ID NO:1, comprising: a) producing Clone 1 (ABV-DEN3ME) and amplifying Clone 1 in *E. coli* cells in culture; b) producing Clone 2 (ABV-DEN3ΔME) and amplifying Clone 2 in *E. coli* cells in culture; c) isolating the amplified Clone 1 and Clone 2 from the cells of (a) and (b), respectively; d) digesting the isolated Clone 1 of (c) with Cla I restriction enzyme to cut out a segment consisting of preM, E, and first 120 bp of NS1; e) digesting the isolated Clone 2 of (c) with Cla I restriction enzyme to linearize Clone 2; f) ligating the linearized Clone 2 of (e) with the segment of (d) to produce a full length DV3 construct; g) digesting the construct of (f) with a restriction enzyme (e.g., SacI, EcoRI or BssHII) to linearize it; and h) contacting the linearized construct of (g) with a T7 RNA polymerase under conditions whereby RNA transcripts are produced from the DV3 construct, thereby producing the infectious RNA molecule. The present invention further provides an infectious RNA molecule produced by this method.

A further aspect of the present invention is a method of producing infectious DV3 virus particles, comprising: a) producing Clone 1 (ABV-DEN3ME) and amplifying Clone 1 in *E. coli* cells in culture; b) producing Clone 2 (ABV-DEN3ΔME) and amplifying Clone 2 in *E. coli* cells in culture; c) isolating the amplified Clone 1 and Clone 2 from the cells of (a) and (b), respectively; d) digesting the isolated Clone 1 of (c) with Cla I restriction enzyme to cut out a segment consisting of preM, E, and first 120 bp of NS1; e) digesting the isolated Clone 2 of (c) with Cla I restriction enzyme to linearize Clone 2; f) ligating the linearized Clone 2 of (e) with the segment of (d) to produce a full length DV3 construct: g) digesting the construct of (f) with a restriction enzyme (e.g., SacI, EcoRI or BssHII) to linearize it; and h) contacting the linearized construct of (g) with a T7 RNA polymerase under conditions whereby RNA transcripts are produced from the DV3 construct; and i) introducing the RNA transcripts of (h) into mammalian cells in culture under conditions whereby infectious DV3 particles are produced, thereby producing infectious DV3 virus particles. The present invention further provides an infectious DV3 virus particle produced by this method.

DETAILED DESCRIPTION OF THE INVENTION

Figure 1:
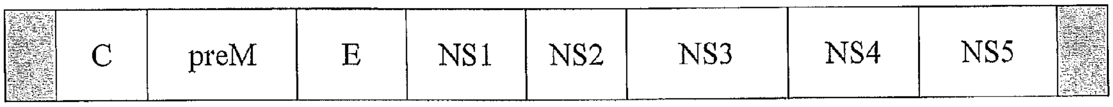
FIG. 1. Schematic diagram of the organization of the dengue virus genome.

As used herein, "a," "an" and "the" can mean one or more than one, depending on the context in which it is used. For example, "a" cell can mean one cell or multiple cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 USPQ 461, 463 (CCPA 1976) (emphasis in the original); see also MPEP §2111.03. Thus, the term "consisting essentially of" when used in a claim of this invention is not intended to be interpreted to be equivalent to "comprising."

The term "consisting essentially of" (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence such that the function of the polynucleotide or polypeptide is not materially altered. The total of ten or less additional nucleotides or amino acids includes the total number of additional nucleotides or amino acids on both ends added together. The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in angiogenesis-stimulating activity of at least about 50% or more as compared to the activity of a polypeptide consisting of the recited sequence.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

The present invention is described in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure that do not depart from the instant invention. Hence, the following description is intended to illustrate some particular embodiments of the invention, and not to exhaustively specify all permutations, combinations and variations thereof.

The present invention provides a dengue 3 virus (DV3) infectious clone that can be used in a variety of therapeutic, vaccine and diagnostic applications. Thus, in one embodiment, the present invention provides an isolated nucleic acid molecule comprising, consisting essentially of or consisting of a nucleotide sequence encoding an infectious RNA molecule encoding a live viral strain of a dengue 3 virus (DV3), wherein said nucleotide sequence is the nucleotide sequence of SEQ ID NO:1 (full length DV3 clone sequence without vector) or a nucleotide sequence having at least 99% identity with the nucleotide sequence of SEQ ID NO:1.

Also provided herein is an isolated, transformed or transfected host cell comprising the nucleic acid molecule of this invention.

In some embodiments, the nucleic acid molecule of this invention can be operatively linked to an RNA polymerase promoter. Nonlimiting examples of an RNA polymerase promoter include T3, T7 and SP6.

The present invention further provides a vector comprising the nucleic acid molecule of this invention. Any suitable vector known in the art can be used to provide the nucleic acid molecule of this invention. Exemplary vectors include but are not limited to plasmids, BACs, YACs, phage, cosmids and viral vectors (e.g., adenovirus, EBV, AAV, baculovirus, herpesvirus, lentivirus, alphavirus and the like).

In some embodiments, the nucleic acid molecule in the vector can be operatively linked to a promoter. In some embodiments, the promoter can be an RNA polymerase promoter. In some embodiments, the vector of this invention can comprise, consist essentially of or consist of the nucleotide sequence of SEQ ID NO:2 (full length DV3 clone sequence in pRS424 vector).

Expression vectors can be designed for expression of polypeptides in prokaryotic or eukaryotic cells. For example, polypeptides can be expressed in bacterial cells such as *E. coli*, insect cells (e.g., the baculovirus expression system), yeast cells, plant cells or mammalian cells. Some suitable host cells are discussed further in Goeddel, *Gene Expression Technology: Methods in Enzymology* 185, Academic Press, San Diego, Calif. (1990). Examples of vectors for expression in the yeast *S. cerevisiae* include pYepSec1 (Baldari et al., (1987) *EMBO J.* 6:229-234), pMFa (Kurj an and Herskowitz, (1982) *Cell* 30:933-943), pJRY88 (Schultz et al., (1987) *Gene* 54:113-123), and pYES2 (Invitrogen Corporation, San Diego, Calif.). Baculovirus vectors available for expression of nucleic acids to produce proteins in cultured insect cells (e.g., Sf9 cells) include the pAc series (Smith et al., (1983) *Mol. Cell. Biol.* 3:2156-2165) and the pVL series (Lucklow, V. A., and Summers, M.d. (1989) *Virology* 170:31-39).

Examples of mammalian expression vectors include pCDM8 (Seed *Nature* 329:840 (1987)) and pMT2PC (Kaufman et al. *EMBO J.* 6:187-195 (1987)). When used in mammalian cells, the expression vector's control functions are often provided by viral regulatory elements. For example, commonly used promoters are derived from polyoma, adenovirus 2, cytomegalovirus and Simian Virus 40.

In addition to the regulatory control sequences discussed above, the recombinant expression vector can contain additional nucleotide sequences. For example, the recombinant expression vector can encode a selectable marker gene to identify host cells that have incorporated the vector.

In another embodiment, the invention features cells, e.g., transformed cells, which contain a nucleic acid molecule or nucleotide sequence of this invention. A "transformed cell" is a cell into which (or into an ancestor of which) has been introduced, by means of recombinant nucleic acid techniques, a nucleic acid of this invention. Both prokaryotic and eukaryotic cells are included, e.g., bacteria, yeast, insect, mouse, rat, human, plant and the like.

The term "transformation" as used herein refers to the introduction of a heterologous nucleic acid into a cell. Transformation of a cell may be stable or transient. The term "transient transformation" or "transiently transformed" refers to the introduction of one or more heterologous nucleic acids into a cell wherein the heterologous nucleic acid is not heritable from one generation to another.

"Stable transformation" or "stably transformed" refers to the integration of the heterologous nucleic acid into the genome of the cell or incorporation of the heterologous nucleic acid into the cell or cells (e.g., via a plasmid) such that the heterologous nucleic acid is heritable across repeated generations. Thus, in one embodiment of the present invention a stably transformed cell is produced.

Transient transformation may be detected, for example, by an enzyme-linked immunosorbent assay (ELISA) or Western blot, which can detect the presence of a peptide or polypeptide encoded by one or more transgene introduced into a cell. Stable transformation of a cell can be detected by, for example, a Southern blot hybridization assay of genomic DNA of the cell with nucleic acid sequences which specifically hybridize with a nucleotide sequence of a transgene introduced into a cell. Stable transformation of a cell can be detected by, for example, a Northern blot hybridization assay of RNA of the cell with nucleic acid sequences which specifically hybridize with a nucleotide sequence of a transgene introduced into a cell. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

Vector DNA can be introduced into prokaryotic or eukaryotic cells via conventional transformation or transfection techniques. Thus, as used herein, the terms "transformation" and "transfection" also refer to a variety of art-recognized techniques for introducing foreign nucleic acids (e.g., DNA) into a host cell, including calcium phosphate or calcium chloride co-precipitation, DEAE-dextran-mediated transfection, lipofection, electroporation, microinjection, DNA-loaded liposomes, lipofectamine-DNA complexes, cell sonication, gene bombardment using high velocity microprojectiles, and viral-mediated transfection. Suitable methods for transforming or transfecting host cells can be found in Sambrook et al. (Molecular Cloning: A Laboratory Manual, 2nd Edition, Cold Spring Harbor Laboratory press (1989)), and other laboratory manuals.

If stable integration is desired, often only a small fraction of cells (in particular, mammalian cells) integrate the foreign DNA into their genome. In order to identify and select integrants, a nucleic acid that encodes a selectable marker (e.g., resistance to antibiotics) can be introduced into the host cells along with the nucleic acid of interest. Preferred selectable markers include those that confer resistance to drugs, such as G418, hygromycin and methotrexate. Nucleic acids encoding a selectable marker can be introduced into a host cell on the same vector as that comprising the nucleic acid of interest or can be introduced on a separate vector. Cells stably transfected with the introduced nucleic acid can be identified by drug selection (e.g., cells that have incorporated the selectable marker gene will survive, while the other cells die). The present invention also provides an isolated infectious RNA molecule encoded by the nucleic acid molecule of claim 1, wherein the infectious RNA molecule encodes a live viral strain of dengue 3 virus. In some embodiments, the RNA molecule can comprise, consist essentially of or consist of the nucleotide sequence of SEQ ID NO:3 (RNA sequence of DV3 clone).

As used herein, "infectious RNA molecule" refers to an RNA molecule that encodes the entire viral genome and is capable of producing infectious virus particles. An examples of an infectious RNA molecule of this invention is an RNA molecule comprising the nucleotide sequence of SEQ ID NO:3.

Also as used herein, "live viral strain of dengue 3 virus" means an infectious strain that is capable of infecting cells and replicating in cells to produce infectious virus particles.

As used herein, the term "nucleic acid," "nucleic acid molecule" and "nucleotide sequence" encompass both RNA and DNA, including cDNA, genomic DNA, synthetic (e.g., chemically synthesized) DNA and chimeras of RNA and DNA. The nucleic acid molecule or nucleotide sequence may be double-stranded or single-stranded. Where single-stranded, the nucleic acid molecule may be a sense strand or an antisense strand. The nucleic acid molecule may be synthesized using oligonucleotide analogs or derivatives (e.g., inosine or phosphorothioate nucleotides). Such oligonucleotides can be used, for example, to prepare nucleic acid molecules or nucleotide sequences that have altered base-pairing abilities or increased resistance to nucleases.

An "isolated nucleic acid" or "isolated nucleotide sequence" is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid or nucleotide sequence includes some or all of the 5' non-coding (e.g., promoter) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant DNA that is part of a hybrid gene encoding an additional polypeptide sequence.

The term "isolated" can refer to a nucleic acid, nucleotide sequence or polypeptide that is substantially free of cellular material, viral material, or culture medium (when produced by recombinant DNA techniques), or chemical precursors or other chemicals (when chemically synthesized). As used herein, the term "isolated nucleic acid" means a nucleic acid separated or substantially free from at least some of the other components of the naturally occurring organism, for example, the cell structural components commonly found associated with nucleic acids in a cellular environment and/or other nucleic acids. Moreover, an "isolated nucleic acid fragment" is a nucleic acid fragment that is not naturally occurring as a fragment and would not be found in the natural state. "Isolated" does not mean that the preparation is technically pure (homogeneous), but it is sufficiently pure to provide the polypeptide or nucleic acid in a form in which it can be used for the intended purpose.

The isolation of nucleic acids can therefore be accomplished by well-known techniques such as cell lysis followed by phenol plus chloroform extraction, followed by ethanol precipitation of the nucleic acids. The nucleic acids of this invention can be isolated from cells according to methods well known in the art for isolating nucleic acids. Alternatively, the nucleic acids of the present invention can be synthesized according to standard protocols well described in the literature for synthesizing nucleic acids. Modifications to the nucleic acids of the invention are also contemplated, provided that the essential structure and function of the peptide or polypeptide encoded by the nucleic acid are maintained.

Furthermore, an "isolated cell" is a cell that has been separated from other components with which it is normally associated in nature. For example, an isolated cell can be a cell in culture medium and/or a cell in a pharmaceutically acceptable carrier of this invention.

The terms "exogenous" and/or "heterologous" as used herein can include a nucleotide sequence that is not naturally occurring in the nucleic acid construct and/or delivery vector (e.g., virus delivery vector) in which it is contained and can also include a nucleotide sequence that is placed into a non-naturally occurring environment and/or non-naturally occurring position relative to other nucleotide sequences (e.g., by association with a promoter or coding sequence with which it is not naturally associated).

The invention also features nucleic acid constructs (e.g., vectors and plasmids) that include a nucleic acid molecule or nucleotide sequence of the invention that is operably linked to a transcription and/or translation control element to enable expression, e.g., expression vectors. By "operably linked" is meant that a selected nucleic acid is positioned adjacent to or within proximity to one or more regulatory elements, e.g., a promoter, which directs transcription and/or translation of the sequence such that the regulatory elements can control transcription and/or translation of the selected nucleic acid.

The nucleic acid molecule of this invention can be part of a recombinant nucleic acid construct comprising any combination of restriction sites and/or functional elements as are well known in the art that facilitate molecular cloning and other recombinant DNA manipulations. Thus, the present invention further provides a recombinant nucleic acid construct comprising a nucleic acid molecule of this invention.

The present invention further provides a vector comprising a nucleic acid molecule of this invention. The vector can be any expression vector (e.g., prokaryotic or eukaryotic) that contains all of the genetic components required for expression of the nucleic acid in cells into which the vector has been introduced, as are well known in the art. The expression vector can be a commercial expression vector or it can be constructed in the laboratory according to standard molecular biology protocols. The nucleic acid molecule and/or vector of this invention can also be in a liposome or a delivery vehicle, which can be taken up by a cell via receptor-mediated or other type of endocytosis.

Further provided herein is a method of producing a nucleic acid molecule comprising a nucleotide sequence encoding an infectious RNA molecule encoding a live viral strain of a dengue 3 virus (DV3), wherein said nucleotide sequence is the nucleotide sequence of SEQ ID NO:1 or a nucleotide sequence having at least 99% identity with the nucleotide sequence of SEQ ID NO:1, comprising: a) producing Clone 1 (ABV-DEN3ME) and amplifying Clone 1 in *E. coli* cells in culture; b) producing Clone 2 (ABV-DEN3ΔME) and amplifying Clone 2 in *E. coli* cells in culture; c) isolating the amplified Clone 1 and Clone 2 from the cells of (a) and (b), respectively; d) digesting the isolated Clone 1 of (c) with Cla I restriction enzyme to cut out a segment consisting of preM, E, and first 120 bp of NS1; e) digesting the isolated Clone 2 of (c) with Cla I restriction enzyme to linearize Clone 2; and f) ligating the linearized Clone 2 of (e) with the segment of (d), thereby producing a nucleic acid molecule comprising a nucleotide sequence encoding an infectious RNA molecule encoding a live viral strain of a dengue 3 virus (DV3), wherein said nucleotide sequence is the nucleotide sequence of SEQ ID NO:1 or a nucleotide sequence having at least 99% identity with the nucleotide sequence of SEQ ID NO:1. Also provided herein is an isolated nucleic acid molecule produced by this method.

Additionally provided herein is a method of producing an infectious RNA molecule encoded by a nucleic acid molecule comprising a nucleotide sequence encoding an infectious RNA molecule encoding a live viral strain of a dengue 3 virus (DV3), wherein said nucleotide sequence is the nucleotide sequence of SEQ ID NO:1 or a nucleotide sequence having at least 99% identity with the nucleotide sequence of SEQ ID NO:1, comprising: a) producing Clone 1 (ABV-DEN3ME) and amplifying Clone 1 in *E. coli* cells in culture; b) producing Clone 2 (ABV-DEN3ΔME) and amplifying Clone 2 in *E. coli* cells in culture; c) isolating the amplified Clone 1 and Clone 2 from the cells of (a) and (b), respectively; d) digesting the isolated Clone 1 of (c) with Cla I restriction enzyme to cut out a segment consisting of preM, E, and first 120 bp of NS1; e) digesting the isolated Clone 2 of (c) with Cla I restriction enzyme to linearize Clone 2; f) ligating the linearized Clone 2 of (e) with the segment of (d) to produce a full length DV3 construct; g) digesting the construct of (f) with a restriction enzyme (e.g., SacI, EcoRI or BssHII) to linearize it; h) contacting the linearized construct of (g) with a T7 RNA polymerase under conditions whereby RNA transcripts are produced from the DV3 construct, thereby producing an infectious RNA molecule encoded by a nucleic acid molecule comprising a nucleotide sequence encoding an infectious RNA molecule encoding a live viral strain of a dengue 3 virus (DV3), wherein said nucleotide sequence is the nucleotide sequence of SEQ ID NO:1 or a nucleotide sequence having at least 99% identity with the nucleotide sequence of SEQ ID NO:1. Also provided herein is an infectious RNA molecule produced by this method.

In further embodiments, the present invention provides a method of producing infectious DV3 virus particles, comprising: a) producing Clone 1 (ABV-DEN3ME) and amplifying Clone 1 in *E. coli* cells in culture; b) producing Clone 2 (ABV-DEN3ΔME) and amplifying Clone 2 in *E. coli* cells in culture; c) isolating the amplified Clone 1 and Clone 2 from the cells of (a) and (b), respectively; d) digesting the isolated Clone 1 of (c) with Cla I restriction enzyme to cut out a segment consisting of preM, E, and first 120 bp of NS1; e) digesting the isolated Clone 2 of (c) with Cla I restriction enzyme to linearize Clone 2; f) ligating the linearized Clone 2 of (e) with the segment of (d) to produce a full length DV3 construct; g) digesting the construct of (f) with a restriction enzyme (e.g., SacI, EcoRI or BssHII) to linearize it; h) contacting the linearized construct of (g) with a T7 RNA polymerase under conditions whereby RNA transcripts are produced from the DV3 construct; and i) introducing the RNA transcripts of (h) into cells in culture under conditions whereby infectious DV3 particles are produced, thereby producing infectious DV3 virus particles Also provided herein is an infectious DV3 virus particle produced by this method.

The examples below are set forth to illustrate the present invention, and are not to be construed as limiting thereof.

EXAMPLES

Example 1

Arbovax DEN3 Infectious Clone System

The full length Dengue serotype 3 virus (DV3) cDNA clone itself is toxic to *E. coli* and cannot be propagated in culture for the purposes of making stock DNA (Messer et al. "Development and characterization of a reverse genetic system for studying dengue virus serotype 3 strain variation and neutralization" *PLoS Negl Trop Dis* 6(2):e1486 (2012): Blaney et al. "Genetically modified, live attenuated dengue virus type 3 vaccine candidates" *Am J Trop Med Hyg* 71(6): 811-821 (2004)).

In the present invention, a 2-clone system has been designed to produce full length infectious DV3. The entirety of the coding sequence plus the 5' and 3' untranslated regions (UTRs) of DV3 have been split up into 2 sub-clones that can be amplified in *E. coli* cells. When specific regions of each sub-clone (FIG. 1) are ligated together, these clones produce the full length coding sequence of DV3. The full length ligated clone is used as a transcription template to produce infectious RNAs in vitro. The RNAs are then transfected into cells (mammalian or insect) and can be assembled into functional, virulent virus. Virus infections from these clones reach a titer of $10^6$ pfu/mL. By splitting the coding sequence into 2 parts, each subclone is stable and can be grown in *E. coli* to produce DNA stocks.

Figure 2:
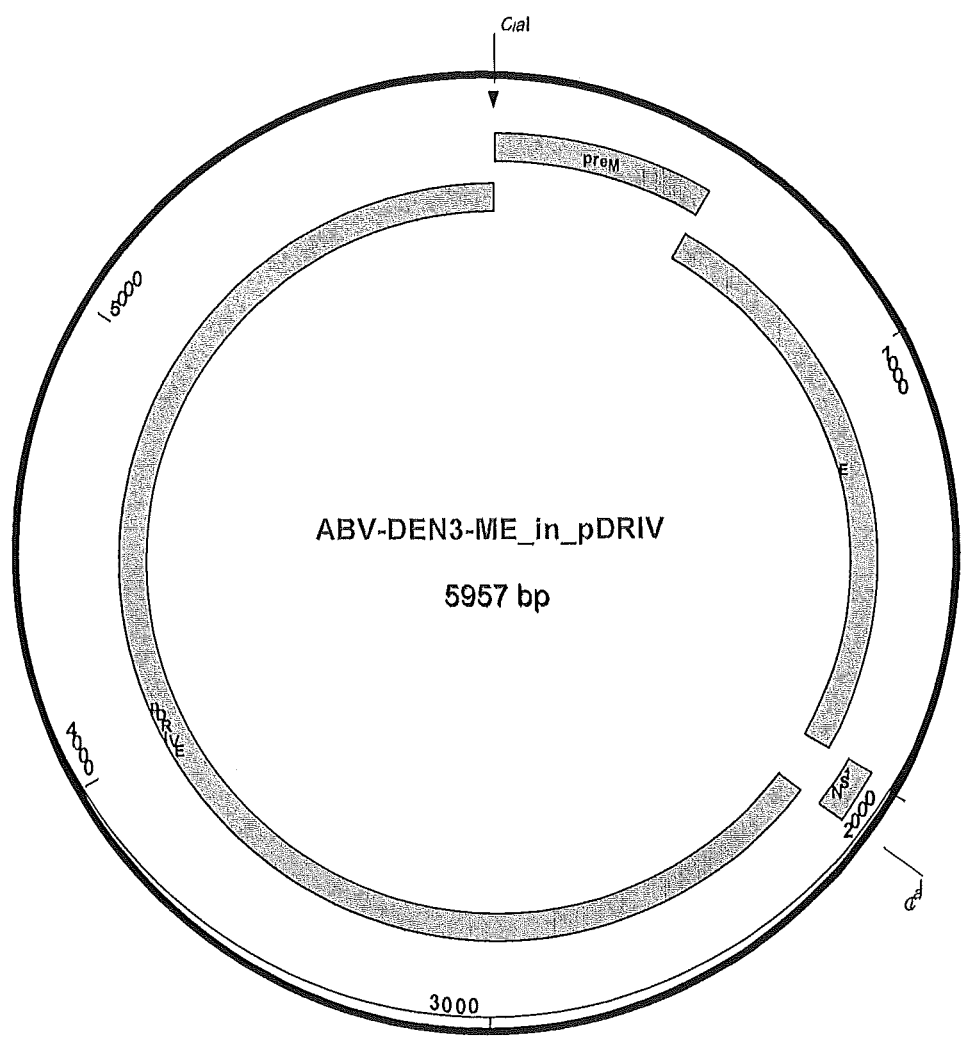
FIG. 2. Clone 1, DEN3 M and E domains in the pDRIVE vector.
Figure 3:
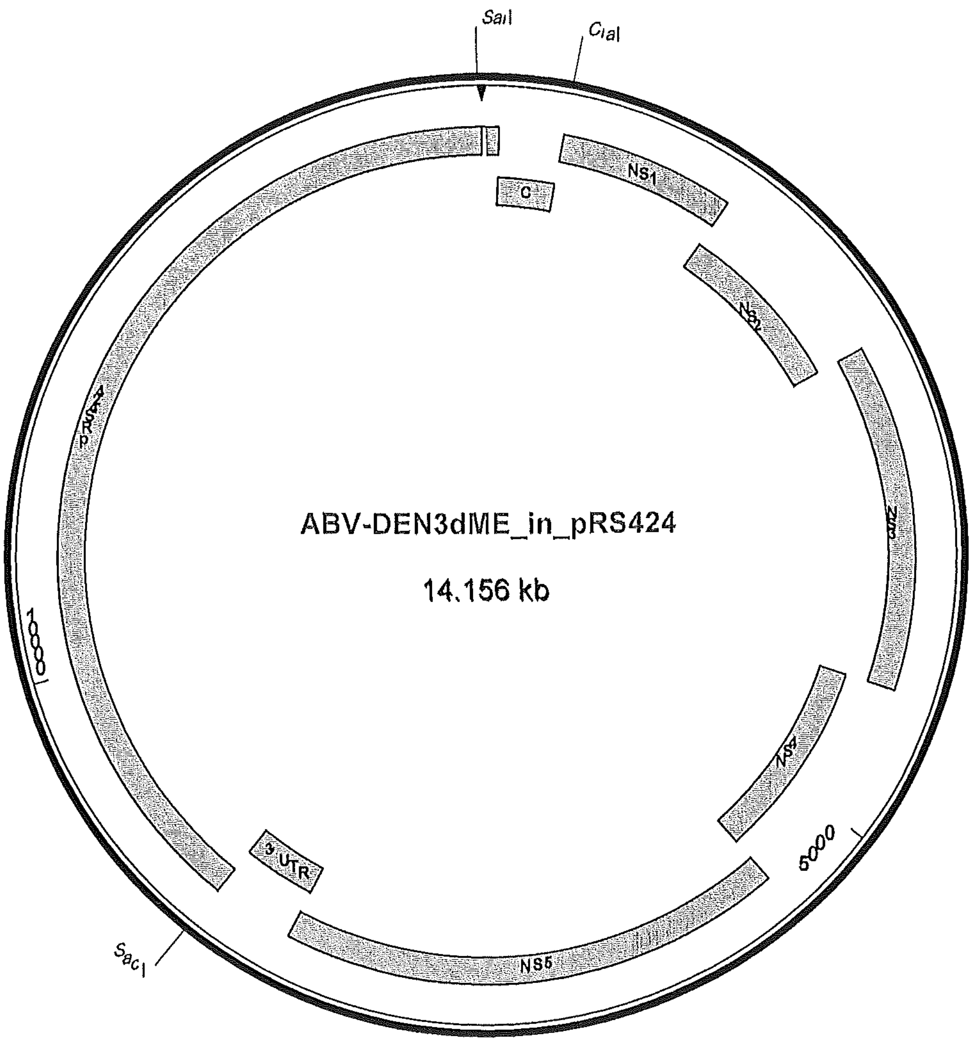
FIG. 3. Clone 2, DEN3ΔM&E in the pRS424 vector.

As shown in FIG. 2, Clone 1 (designated ABV-DEN3ME) contains the coding sequence for the membrane protein precursor (preM) and envelope (E) domains as well as the first 120 base pairs of nonstructural protein 1 (NS1) of DV3 in the vector pDRIVE. As shown in FIG. 3, Clone 2 (designated ABV-DEN3ΔME) has the 5' UTR, Capsid (C), all non-structural protein sequences (NS1-5; minus the first 120 bp of NS1) and the 3' UTR in the vector pRS424.

Clone 1 (ABV-DEN3ME) containing the preM and E domains of DEN3 was created by purifying viral RNA from DV3 strain UNC3001 (GenBank® Database Accession No. JQ411814) and amplifying those regions by reverse transcription polymerase chain reaction (RT-PCR). The resulting piece of DNA was cloned into the pDRIVE vector (Qiagen, Germantown, Md.) using the Qiagen PCR Cloning kit. One modification was made to the pDRIVE vector; the Cla I site at position 2304 was removed by substituting a thymidine with a cytosine so that only DV3 M and E domains would be removed from the vector upon digestion with Cla I.

The remaining pieces of the DV3 genome, generated from DV3 strain CH53489 (GenBank® Database Accession No. JQ411814), were inserted into the pRS424 vector (ATCC Accession No. 77105). A Cla I site was added at nucleotide position 433 from which the DEN3 M and E and the first 120 bp of NS1 were removed. Base pairs at positions 2554-2559 were removed by PCR based site-directed mutagenesis in order to 1) remove a stop codon; and 2) preserve the proper length of the E domain. Nucleotide sequence numbering is based on the nucleotide sequence of SEQ ID NOs:2 and 3 in the attached Sequence Listing.

Both of these constructs can be stably grown in *E. coli* cells. To make infectious virus, both clones are digested with Cla I. The digest cuts out the preM, E, and first 120 bp of NS1, which is then gel purified and ligated to the Cla I-linearized second clone. After ligation, the full length DV3 construct in the pRS424 vector is linearized with a Sac I digest and T7 RNA polymerase is used to generate RNA transcripts. Because the insert is not unidirectional the Cla I insert can be incorporated in both + strand and – strand orientations but only the + sense RNA will make infectious mRNA. The RNA transcripts are then transfected into mammalian (e.g., African Green monkey, Vero) cells or insect cells (e.g., C636 mosquito cells) in culture via, e.g., electroporation, wherein the messenger RNA is transcribed and translated into viral proteins, the RNA is replicated to produce viral RNA genomic molecules and infectious DV3 particles are assembled in the cells that can be harvested from the cell culture supernatant.

Average titers of approximately $10^4$ and $10^5$ plaque forming units (PFU)/ml have been achieved in Vero cells (mammalian cells) and C6/36 mosquito cells (insect cells), respectively.

All publications, patent applications and non-patent references are herein incorporated by reference to the same extent as if each individual publication or patent application or refernce was specifically and individually indicated to be incorporated by reference.

Although the foregoing invention has been described in some detail by way of illustration and example for purposes of clarity of understanding, it will be obvious that certain changes and modifications may be practiced within the scope of the list of the foregoing embodiments and the appended claims.

What is claimed is:

1. An isolated nucleic acid molecule comprising a nucleotide sequence encoding an infectious RNA molecule encoding a live viral strain of a dengue 3 virus (DV3), wherein said nucleotide sequence is the nucleotide sequence of SEQ ID NO: 1.

2. A vector comprising the nucleic acid molecule of claim 1.

3. The nucleic acid molecule of claim 1, operably linked to an RNA polymerase promoter.

4. A vector comprising the nucleic acid molecule of claim 3.

5. A vector comprising the nucleotide sequence of SEQ ID NO:2.

6. An isolated infectious RNA molecule comprising the nucleotide sequence of SEQ ID NO:3.

7. An isolated host cell that is transformed or transfected to comprise the isolated infectious RNA molecule of claim 6.

* * * * *

SEQUENCE LISTING

```
<160> NUMBER OF SEQ ID NOS: 3

<210> SEQ ID NO 1
<211> LENGTH: 10708
<212> TYPE: DNA
<213> ORGANISM: Dengue virus type 3

<400> SEQUENCE: 1

agttgttagt ctacgtggac cgacaagaac agtttcgact cggaagcttg cttaacgtag      60

tgctgacagt tttttattag agagcagatc tctgatgaac aaccaacgga aaaagacggg     120

aaaaccgtct atcaatatgc tgaaacgcgt gagaaaccgt gtgtcaactg gatcacagtt     180

ggcgaagaga ttctcaagag gattgctgaa cggccaagga ccaatgaagt tggttatggc     240

gttcatagct ttcctcagat ttctagccat tccaccaaca gcaggagtct tggctagatg     300

gggaaccttc aagaagtcag gggctattaa ggtcctaaaa ggcttcaaga aggagatttc     360

aaacatgctg agcattatca acaaaaggaa aaagacatcg ctctgtctca tgatgatgtt     420

accagcaaca cttatcgatc acttgacttc acgagatgga gagccgcgca tgattgtggg     480

gaagaatgaa agaggaaaat cccaactttt taagacagcc tctggaatta acatgtgcac     540

actcatagcc atggacttgg gagagatgtg tgatgacgcg gtcacttaca aatgccccca     600

cattaccgaa gtggaacctg aagacattga ctgctggtgc aaccttacat caacatgggt     660

gacttatgga acgtgcaacc aagctggaga gcatagacgc gacaaaagat cagtggcgtt     720

agctcctcat gtcggcatgg gactggacac acgcacccaa acctggatgt cggctgaagg     780

agcttggaga caagtcgaga gggtagagac atgggccctc aggcacccag ggttcaccat     840

actagcccta tttcttgccc attacatagg cacttccttg acccagaagg tggttatttt     900

tatactacta atgctggtca ccccatccat gacaatgaga tgtgtgggaa taggaaacag     960

agattttgtg gaaggtctat caggagctac gtgggttgac gtggtgctcg agcacggggg    1020

gtgtgtgact accatggtta agaacaagcc cacgctggat atagagcttc agaagaccga    1080

ggccacccaa ctggcgaccc taaggaagct atgcattgag gggaaaatta ccaacataac    1140

aactgactca agatgtccta cccaagggga agcggttttg cctgaggagc aggaccagaa    1200

ctacgtgtgt aagcatacat acgtagacag aggctggggg aacggttgtg gcttgtttgg    1260

caagggaagc ttggtaacgt gtgcgaaatt tcaatgcctg gaaccaatgg agggaaaagt    1320

ggtgcaatat gagaacctca aatacaccgt catcattaca gtgcacacag gagaccaaca    1380

ccaggtagga aatgaaatgc agggagtcac ggctgagata acacctcagg catcaaccac    1440
```

-continued

```
tgaagccatc ttgcctgaat atggaaccct tgggctagaa tgctcaccac ggacaggttt   1500
ggatttcaat gaaatgatct tactaacaat gaagaacaaa gcatggatgg tacatagaca   1560
atggtttttt gacctacctc taccatggac atcaggagct acaacagaaa cgccaacttg   1620
gaacaggaag gagcttcttg tgacattcaa aaacgcacat gcgaaaaaac aagaagtagt   1680
cgtccttgga tcgcaagagg gagcaatgca taccgcactg acaggagcca cagaaatcca   1740
aaactcagga ggcacaagca tttttgcggg gcacttaaaa tgtagactta agatggacaa   1800
attggaactc aaggggatga gctatgcaat gtgcacgaat acctttgtgt tgaagaaaga   1860
agtctcagaa acgcagcatg ggacaatact cattaaggtc gagtacaaag gggaagatgc   1920
accttgcaag attcctttct ccacagagga tggacaaggg aaagctcaca atggcagacc   1980
gatcacagcc aacccagtgg tgactaagaa ggaggagccc gtcaatattg aggctgagcc   2040
tccttttggg gaaagcaata tagtaattgg aattggagac aacgccttga aaatcaactg   2100
gtacaagaag ggaagctcta ttgggaagat gttcgaggcc actgccagag gtgcaaggcg   2160
catggccatc ttgggagaca cagcttggga ctttggatca gtgggtggtg ttctgaactc   2220
attaggcaaa atggtgcacc aaatattcgg aagtgcttac acagccctat tcagtggagt   2280
ctcttgggtg atgaaaattg gaataggtgt tctcttgact tggatagggt tgaattcaaa   2340
aaacacatcc atgtcatttt catgcattgc gataggaatc attacactct atctgggagc   2400
tgtggtacaa gctgacatgg ggtgtgtcat aaactggaaa ggcaaagaac tcaaatgtgg   2460
aagtggaatt ttcgtcacca acgaggtcca tacctggaca gagcaataca aatttcaagc   2520
agactccccc aatcgattgg cgacagccat tgcaggcgcc tgggaaaatg gagtctgtgg   2580
aatcaggtca acaaccagaa tggagaatct attgtggaag caaatagcca atgaactgaa   2640
ctacatatta tgggaaaaca acatcaaatt aacggtagtg gtgggcgaca taattggggt   2700
cttagagcaa gggaaaagaa cactaacacc acaacccatg gagctaaaat attcatggaa   2760
aacatgggga aaagcaaaaa tagtgacagc tgaaacacaa aattcctctt tcataataga   2820
tgggccaaac acaccggagt gtccaagtgc ctcaagagca tggaatgtgt gggaggtgga   2880
agattacggg tttggagtct tcacaaccaa catatggctg aaactccgag aggtgtacac   2940
ccaattgtgc gaccataggc taatgtcagc agccgtcaaa gatgagaggg ccgtgcatgc   3000
cgacatgggc tattggatag aaagccaaaa gaatggaagt tggaagctag aaaaagcatc   3060
cctcatagag gtaaaaacct gcacttggcc aaaatcacac actctttgga gtaatggtgt   3120
actagagagt gacatgatca tcccaaagag tctaactggt cctatttcgc aacacaacca   3180
caggcccggg taccacaccc aaacggcagg accctggcac ttgggaaaat tggagctgga   3240
cttcaactat tgtgaaggaa caacagttgt catcacagaa aactgtggga caagaggccc   3300
atcattgaga acaacaacag tgtcggggaa gttgatacac gaatggtgtt gccgctcgtg   3360
cacacttcct cccttgcgat acatgggaga agacggctgc tggtatggca tggaaattag   3420
acccatcaat gagaaagaag agaacatggt aaagtcttta gcctcagcag ggagtggaaa   3480
ggtggacaac ttcacaatgg gtgtcctgtg tttggcaatc ctcttcgaag aggtgatgag   3540
aggaaaattt gggaaaaaac acatgattgc aggggttctc ctcacgtttg tgctccttct   3600
ctcagggcaa ataacatgga gagatatggc gcacacactc ataatgattg ggtccaacgc   3660
ttctgacagg atgggaatgg gcgttaccta cctagcttta attgcaacat ttaaaatcca   3720
gccattcttg gctttgggat tcttcctgag gaaactgaca tctagagaaa atttattgct   3780
gggagttggg ttggccatgg caacaacgtt acaactgcca gaggacattg aacaaatggc   3840
```

-continued

```
gaatggaatt gctctggggc tcatggctct taaactgata acacaatttg agacatacca   3900
gttatggacg gcattagtct ccctaacgtg ttcaaataca attttcacgt tgactgttgc   3960
ctggagaaca gccaccttga ttctggccgg agtttcgctt ttgccagtgt gccagtcttc   4020
gagcatgagg aaaacagatt ggctcccaat ggctgtggca gctatgggag ttccaccctt   4080
accacttttc atcttcagct tgaaagatac actcaaaagg agaagctggc cactgaatga   4140
gggggtgatg gctgttgggc ttgtgagcat tctagctagc tctctcctta ggaatgatgt   4200
gcccatggct ggaccattag tggccggggg cttgctgata gcgtgctacg tcataactgg   4260
cacgtcagcg gacctcactg tagaaaaagc agcagatgta acatgggagg aagaggctga   4320
gcaaacagga gtgtcccaca atttgatgat cacagttgat gatgatggaa caatgagaat   4380
aaaagatgat gagactgaga acatcctaac agtgctctta aaaacagcat tactaatagt   4440
atcaggcatc tttccatatt ccatacccgc cacactgttg gtctggcata cttggcaaaa   4500
gcaaacccaa agatctggcg ttctatggga cgtacccagc cccccagaaa cacagaaagc   4560
agaactggaa gagggggtct ataggatcaa acagcaagga atttttggga aaacccaagt   4620
gggggttgga gtacagaaag aaggagtctt ccataccatg tggcacgtca caagaggggc   4680
agtgttgacg cacaatggga aaagattgga accaaactgg gccagcgtga aaaaagatct   4740
gatttcatac ggaggaggat ggagattgag tgcacaatgg caaaagggag aggaggtgca   4800
ggttattgcc gtagagcccg ggaagaaccc aaagaacttt caaaccatgc cgggcatttt   4860
tcagacaaca acaggggaaa taggagcaat tgcactagac ttcaagcctg gaacttcagg   4920
atctcctatc ataaacagag agggaaaggt agtgggactg tatggcaatg gagtggttac   4980
aaagaatggt ggctacgtca gtggaatagc gcaaacaaat gcagaaccag acggaccgac   5040
accggagttg gaagaggaga tgttcaaaaa gcgaaatcta accataatgg atcttcatcc   5100
tgggtcagga aagacgcgga aatatcttcc agctatcgtc agagaagcaa tcaagagacg   5160
cttaagaact ctaatcttgg caccaacaag ggtggttgca gctgagatgg aagaagcatt   5220
gaaagggctc ccaataaggt atcaaacaac tgcaacaaaa tctgaacaca caggaaggga   5280
gattgttgat ctaatgtgcc acgcaacgtt cacaatgcgc ttgctatcac cagtcagggc   5340
tccaaattac aatttgataa taatggatga ggcccatttc acagatccag ccagtatagc   5400
ggctagaggg tacatatcaa ctcgtgtagg aatgggagag gcagctgcaa tcttcatgac   5460
agcaacaccc cctggaacag ccgatgcctt tcctcagagc aacgctccaa ttcaagatga   5520
agaaagggat atcccggaac gctcatggaa ttcaggcaat gaatggatta ccgactttgt   5580
tgggaagacg gtgtggtttg tccccagcat caaagccgga aatgacatag caaactgctt   5640
gcggaaaaat ggaaaaaagg tcattcaact tagtaggaag acttttgata cagaatatca   5700
aaagaccaaa ctgaatgatt gggacttcgt ggtgacaaca gacatttcag aaatgggagc   5760
caactttaaa gcagatagag tgatcgaccc aagaagatgt ctcaagccag tgattttgac   5820
agatggaccc gagcgggtga tcctggctgg accaatgcca gtcactgcag cgagcgctgc   5880
gcaaaggaga gggagagttg gcaggaaccc acaaaaagaa aatgaccagt acatattcac   5940
gggccagcct ctcaacaatg acgaagacca tgctcactgg acagaagcaa aaatgctgct   6000
ggacaacatc aacacaccag aagggattat accagctctc tttgaaccag aaagggagaa   6060
gtcagccgcc atagacggtg aataccgcct gaagggtgag tccaggaaga ccttcgtgga   6120
actcatgagg aggggtgacc tcccagtttg gctagcccat aaagtagcat cagaagggat   6180
```

-continued caaatataca gatagaaaat ggtgctttga tggagaacgt aataatcaaa ttttagagga 6240
gaacatggat gtggaaatct ggacaaagga aggagaaaag aaaaaattga gacctaggtg 6300
gcttgatgcc cgcacttatt cagatccctt ggcactcaag gaattcaagg attttgcagc 6360
tggcagaaag tcaatcgccc ttgatcttgt gacagaaata ggaagagtgc cttcacattt 6420
agcccacaga acgagaaacg ccctggacaa tttggtgatg ctgcacacgt cagaacatgg 6480
cggtagggcc tacaggcatg cagtggagga actaccagaa acaatggaaa cactcctact 6540
cttgggactc atgatcttgt taacaggtgg agcaatgctg ttcttgatat caggtaaagg 6600
gattggaaag acttcaatag gactcatctg tgtaattgct tccagtggca tgttatggat 6660
ggccgatgtc ccacttcaat ggatcgcgtc ggctatagtc ctggaatttt tcatgatggt 6720
gttgcttata ccagaaccag aaaagcagag aactccccaa gacaaccaac tcgcatatgt 6780
cgtgataggc atacttacac tggctgcaat agtagcagcc aatgaaatgg gactgttgga 6840
aactacaaag agagatttag gaatgtctaa agaaccaggt gttgtttctc caaccagcta 6900
tttagatgta gacttgcacc cagcatcagc ctggacattg tacgctgtgg ccacaacagt 6960
aataacacca atgttgagac ataccataga gaattccaca gcaaatgtgt ccctggcagc 7020
tatagctaac caggcagtgg tcctgatggg cttagacaaa ggatggccaa tatcgaaaat 7080
ggacttaggc gtaccactac tggcactggg ctgctattca caagtgaacc cactgactct 7140
cacagcggca gtacttttgc tagctacaca ttatgctatt ataggtccag gattgcaggc 7200
aaaagccact cgtgaagctc aaaaaaggac agctgctgga ataatgaaga atccaacggt 7260
ggatgggata atgacaatag acctagatcc tgtaatatac gattcaaaat tcgaaaagca 7320
actaggacag gttatgctcc tagttctgtg tgcagttcaa cttttgttaa tgagaacatc 7380
atgggccttg tgtgaagctc taaccctagc cacaggacca ataacaacac tctgggaagg 7440
atcacctgga aagttttgga acaccacgat agctgtttcc atggctaaca tctttagagg 7500
gagctattta gcaggagctg ggcttgcttt ttctatcatg aaatcagttg gaacaggaaa 7560
gagaggaacg gggtcacaag gcgaaacctt aggagaaaag tggaaaaaga aattaaatca 7620
gttatcccgg aaagagtttg acctttacaa gaaatctgga atcactgaag tggatagaac 7680
agaagccaaa gaagggttga aaagaggaga aataacacgt catgccgtgt ccagaggcag 7740
cgcaaaactt caatggttcg tggagaggaa catggtcatt cccgaaggaa gagtcataga 7800
cttaggctgt ggaagaggag gctggtcata ttactgcgca ggattgaaaa aagttacaga 7860
agtgcgagga tacacaaaag gcggcccagg acacgaagaa ccagtaccta tgtctacata 7920
cggatggaac atagtcaagt taatgagtgg aaaggatgtg ttttatctcc cacctgaaaa 7980
gtgtgacacc ctattgtgtg acattggaga atcttcacca agcccaacag tggaagaaag 8040
cagaactata agagttttga agatggttga accatggcta aaaaataacc agttttgcat 8100
taaagtatta aacccttaca tgccaactgt gattgagcac ctagaaagac tacaaaggaa 8160
acatggagga atgcttgtga gaaatccact ctcacgaaac tccacgcacg aaatgtactg 8220
gatatccaat ggtaccggca acatcgtctc ttcagtcaac atggtatcca gattgctact 8280
gaacagattt acaatgacac acaggagacc caccatagag aaagatgtgg atttgggagc 8340
aggaacccga catgtcaatg cggaaccaga aacacccaat atggacgtca ttggagaaag 8400
aataaaaagg atcaaggagg agcataattc aacatggcac tatgatgatg aaaatcctta 8460
caaaacgtgg gcttaccatg gatcctatga agtcaaagcc acaggctcag cctcctccat 8520
gataaatgga gtcgtgaaac tcctcacaaa accatgggat gtggtgccca tggtgataca 8580

```
gatggcaatg acagatacaa ctccatttgg gcggcaaaga gttttcaaag agaaagtgga   8640
caccaggaca cccaggccca tgccagggac aagaaaggtt atggagatca cagcggaatg   8700
gctttggaga accctgggaa ggaacaaaag acccagattg tgcacaaggg aagagttcac   8760
aaaaaaggtc agaaccaacg cggctatggg tgccgttttc acagaggaga accaatggga   8820
tagtgcgaga gctgctgttg aggacgagga attctggaaa cttgtggaca gagaacgtga   8880
actccacaaa ttgggcaagt gtggaagctg cgtctacaac atgatgggca agagagagaa   8940
gaaacttgga gagtttggca aagcaaaagg cagtagagct atatggtaca tgtggttggg   9000
agccaggtac cttgagttcg aggcactcgg attcttaaat gaagaccact ggttctcgcg   9060
tgaaaactct tacagtggag tagaaggaga aggactgcac aagctgggat acattttaag   9120
agatatttcc aagatacccg gaggagctat gtatgctgat gacacagctg gttgggacac   9180
aagaataaca gaagatgacc tgcacaatga ggaaaaaatc acacagcaaa tggaccctga   9240
acacagacag ttagcgaacg ccatattcaa gctcacatac caaaacaaag tggtcaaagt   9300
tcaacgacca actccaaaag gcacggtaat ggacatcata tctaggaaag accaaagagg   9360
cagtggacag gtggggactt atggtctgaa tacattcacc aacatggaag cccagttagt   9420
cagacagatg gaaggagaag gcgtgttgtc gaaggcagac cttgagaatc ctcatctgct   9480
agagaagaaa atcacacaat ggttggaaac caaaggagtg gagaggttaa aaagaatggc   9540
tatcagtggg gatgattgcg tagtgaaacc gatcgacgac aggtttgcca atgccctgct   9600
tgccctgaac gatatgggaa aggttaggaa ggacatacct caatggcagc catcaaaggg   9660
ttggcatgat tggcaacagg tccctttctg ctcccaccac tttcatgaac tgatcatgaa   9720
agatggaaga aagttggtgg ttccctgcag accccaggac gaactaatag gaagagcgag   9780
aatctctcaa ggagcaggat ggagccttaa agaaactgca tgtctaggga aagcctacgc   9840
tcaaatgtgg agtctcatgt attttcacag aagagatctt agactagcat ccaacgccat   9900
atgttcagca gtaccagtcc attgggtccc tacaagcaga acgacatggt ctattcatgc   9960
tcaccatcag tggatgacta cagaagacat gcttactgtc tggaacaggg tgtggataga  10020
ggacaatcca tggatggaag acaaaactcc agtcacaact tgggaagatg ttccatacct  10080
agggaagaga gaagaccaat ggtgcggatc actcatcggt ctcacttcca gagcaacctg  10140
ggcccagaac atactcacag caatccaaca agtgagaagc cttataggca atgaagagtt  10200
tctggactac atgccttcga tgaagagatt caagaaggag gaggagtcag agggagccat  10260
ttggtaaacg gaggaagtaa aaaagaggca cactgtcagg ccaccttaag ccacagtacg  10320
gaagaagctg tgcagcctgt gagccccgtc caaggacgtt aaaagaagaa gtcaggccca  10380
aaagccacgg tttgagcaaa ccgtgctgcc tgtagctccg tcgtggggac gtaaagcctg  10440
ggaggctgca aactgtggaa gctgtacgca cggtgtagca gactagcggt tagaggagac  10500
ccctcccatg acacaacgca gcagcggggc ccgagcactg agggaagctg tacctccttg  10560
caaaggacta gaggttagag gagacccccc gcaaacaaaa acagcatatt gacgctggga  10620
gagaccagag atcctgctgt ctcctcagca tcattccagg cacagaacgc cagaaaatgg  10680
aatggtgctg ttgaatcaac aggttctc                                     10708
```

<210> SEQ ID NO 2
<211> LENGTH: 16254
<212> TYPE: DNA
<213> ORGANISM: Artificial
<220> FEATURE:

-continued

<223> OTHER INFORMATION: DV3/pRS424 construct

<400> SEQUENCE: 2

```
agttgttagt ctacgtggac cgacaagaac agtttcgact cggaagcttg cttaacgtag     60
tgctgacagt tttttattag agagcagatc tctgatgaac aaccaacgga aaaagacggg    120
aaaaccgtct atcaatatgc tgaaacgcgt gagaaaccgt gtgtcaactg gatcacagtt    180
ggcgaagaga ttctcaagag gattgctgaa cggccaagga ccaatgaagt tggttatggc    240
gttcatagct ttcctcagat ttctagccat tccaccaaca gcaggagtct tggctagatg    300
gggaaccttc aagaagtcag gggctattaa ggtcctaaaa ggcttcaaga aggagatttc    360
aaacatgctg agcattatca acaaaaggaa aaagacatcg ctctgtctca tgatgatgtt    420
accagcaaca cttatcgatc acttgacttc acgagatgga gagccgcgca tgattgtggg    480
gaagaatgaa agaggaaaat cccaactttt taagacagcc tctggaatta acatgtgcac    540
actcatagcc atggacttgg gagagatgtg tgatgacgcg gtcacttaca aatgccccca    600
cattaccgaa gtggaacctg aagacattga ctgctggtgc aaccttacat caacatgggt    660
gacttatgga acgtgcaacc aagctggaga gcatagacgc gacaaaagat cagtggcgtt    720
agctcctcat gtcggcatgg gactggacac acgcacccaa acctggatgt cggctgaagg    780
agcttggaga caagtcgaga gggtagagac atgggccctc aggcacccag ggttcaccat    840
actagcccta tttcttgccc attacatagg cacttccttg acccagaagg tggttatttt    900
tatactacta atgctggtca ccccatccat gacaatgaga tgtgtgggaa taggaaacag    960
agattttgtg gaaggtctat caggagctac gtgggttgac gtggtgctcg agcacggggg   1020
gtgtgtgact accatggtta agaacaagcc cacgctggat atagagcttc agaagaccga   1080
ggccacccaa ctggcgaccc taaggaagct atgcattgag gggaaaatta ccaacataac   1140
aactgactca agatgtccta cccaagggga agcggttttg cctgaggagc aggaccagaa   1200
ctacgtgtgt aagcatacat acgtagacag aggctggggg aacggttgtg gcttgtttgg   1260
caagggaagc ttggtaacgt gtgcgaaatt tcaatgcctg gaaccaatgg agggaaaagt   1320
ggtgcaatat gagaacctca aatacaccgt catcattaca gtgcacacag gagaccaaca   1380
ccaggtagga aatgaaatgc agggagtcac ggctgagata acacctcagg catcaaccac   1440
tgaagccatc ttgcctgaat atggaaccct tgggctagaa tgctcaccac ggacaggttt   1500
ggatttcaat gaaatgatct tactaacaat gaagaacaaa gcatggatgg tacatagaca   1560
atggtttttt gacctacctc taccatggac atcaggagct acaacagaaa cgccaacttg   1620
gaacaggaag gagcttcttg tgacattcaa aaacgcacat gcgaaaaaac aagaagtagt   1680
cgtccttgga tcgcaagagg gagcaatgca taccgcactg acaggagcca cagaaatcca   1740
aaactcagga ggcacaagca tttttgcggg gcacttaaaa tgtagactta agatggacaa   1800
attggaactc aaggggatga gctatgcaat gtgcacgaat acctttgtgt tgaagaaaga   1860
agtctcagaa acgcagcatg ggacaatact cattaaggtc gagtacaaag gggaagatgc   1920
accttgcaag attcctttct ccacagagga tggacaaggg aaagctcaca atggcagacc   1980
gatcacagcc aacccagtgg tgactaagaa ggaggagccc gtcaatattg aggctgagcc   2040
tccttttggg gaaagcaata tagtaattgg aattggagac aacgccttga aaatcaactg   2100
gtacaagaag ggaagctcta ttgggaagat gttcgaggcc actgccagag gtgcaaggcg   2160
catggccatc ttgggagaca cagcttggga ctttggatca gtgggtggtg ttctgaactc   2220
attaggcaaa atggtgcacc aaatattcgg aagtgcttac acagccctat tcagtggagt   2280
```

```
ctcttgggtg atgaaaattg gaataggtgt tctcttgact tggatagggt tgaattcaaa   2340
aaacacatcc atgtcatttt catgcattgc gataggaatc attacactct atctgggagc   2400
tgtggtacaa gctgacatgg ggtgtgtcat aaactggaaa ggcaaagaac tcaaatgtgg   2460
aagtggaatt ttcgtcacca acgaggtcca tacctggaca gagcaataca aatttcaagc   2520
agactccccc aatcgattgg cgacagccat tgcaggcgcc tgggaaaatg gagtctgtgg   2580
aatcaggtca acaaccagaa tggagaatct attgtggaag caaatagcca atgaactgaa   2640
ctacatatta tgggaaaaca acatcaaatt aacggtagtg gtgggcgaca taattggggt   2700
cttagagcaa gggaaaagaa cactaacacc acaacccatg gagctaaaat attcatggaa   2760
aacatgggga aaagcaaaaa tagtgacagc tgaaacacaa aattcctctt tcataataga   2820
tgggccaaac acaccggagt gtccaagtgc ctcaagagca tggaatgtgt gggaggtgga   2880
agattacggg tttggagtct tcacaaccaa catatggctg aaactccgag aggtgtacac   2940
ccaattgtgc gaccataggc taatgtcagc agccgtcaaa gatgagaggg ccgtgcatgc   3000
cgacatgggc tattggatag aaagccaaaa gaatggaagt tggaagctag aaaaagcatc   3060
cctcatagag gtaaaaacct gcacttggcc aaaatcacac actctttgga gtaatggtgt   3120
actagagagt gacatgatca tcccaaagag tctaactggt cctatttcgc aacacaacca   3180
caggcccggg taccacaccc aaacggcagg accctggcac ttgggaaaat tggagctgga   3240
cttcaactat tgtgaaggaa caacagttgt catcacagaa aactgtggga caagaggccc   3300
atcattgaga acaacaacag tgtcggggaa gttgatacac gaatggtgtt gccgctcgtg   3360
cacacttcct cccttgcgat acatgggaga agacggctgc tggtatggca tggaaattag   3420
acccatcaat gagaaagaag agaacatggt aaagtcttta gcctcagcag ggagtggaaa   3480
ggtggacaac ttcacaatgg gtgtcctgtg tttggcaatc ctcttcgaag aggtgatgag   3540
aggaaaattt gggaaaaaac acatgattgc aggggttctc ctcacgtttg tgctccttct   3600
ctcagggcaa ataacatgga gagatatggc gcacacactc ataatgattg ggtccaacgc   3660
ttctgacagg atgggaatgg gcgttaccta cctagcttta attgcaacat ttaaaatcca   3720
gccattcttg gctttgggat tcttcctgag gaaactgaca tctagagaaa atttattgct   3780
gggagttggg ttggccatgg caacaacgtt acaactgcca gaggacattg aacaaatggc   3840
gaatggaatt gctctggggc tcatggctct taaactgata acacaatttg agacatacca   3900
gttatggacg gcattagtct ccctaacgtg ttcaaataca attttcacgt tgactgttgc   3960
ctggagaaca gccaccttga ttctggccgg agtttcgctt ttgccagtgt gccagtcttc   4020
gagcatgagg aaaacagatt ggctcccaat ggctgtggca gctatgggag ttccaccctt   4080
accactttttc atcttcagct tgaaagatac actcaaaagg agaagctggc cactgaatga   4140
gggggtgatg gctgttgggc ttgtgagcat tctagctagc tctctcctta ggaatgatgt   4200
gcccatggct ggaccattag tggccggggg cttgctgata gcgtgctacg tcataactgg   4260
cacgtcagcg gacctcactg tagaaaaagc agcagatgta acatgggagg aagaggctga   4320
gcaaacagga gtgtcccaca atttgatgat cacagttgat gatgatggaa caatgagaat   4380
aaaagatgat gagactgaga acatcctaac agtgctctta aaaacagcat tactaatagt   4440
atcaggcatc tttccatatt ccatacccgc cacactgttg gtctggcata cttggcaaaa   4500
gcaaacccaa agatctggcg ttctatggga cgtacccagc cccccagaaa cacagaaagc   4560
agaactggaa gagggggtct ataggatcaa acagcaagga atttttggga aaacccaagt   4620
```

-continued gggggttgga gtacagaaag aaggagtctt ccataccatg tggcacgtca caagaggggc 4680
agtgttgacg cacaatggga aaagattgga accaaactgg gccagcgtga aaaaagatct 4740
gatttcatac ggaggaggat ggagattgag tgcacaatgg caaaagggag aggaggtgca 4800
ggttattgcc gtagagcccg ggaagaaccc aaagaacttt caaaccatgc cgggcatttt 4860
tcagacaaca acaggggaaa taggagcaat tgcactagac ttcaagcctg gaacttcagg 4920
atctcctatc ataaacagag agggaaaggt agtgggactg tatggcaatg gagtggttac 4980
aaagaatggt ggctacgtca gtggaatagc gcaaacaaat gcagaaccag acggaccgac 5040
accggagttg gaagaggaga tgttcaaaaa gcgaaatcta accataatgg atcttcatcc 5100
tgggtcagga aagacgcgga aatatcttcc agctatcgtc agagaagcaa tcaagagacg 5160
cttaagaact ctaatcttgg caccaacaag ggtggttgca gctgagatgg aagaagcatt 5220
gaaagggctc ccaataaggt atcaaacaac tgcaacaaaa tctgaacaca caggaaggga 5280
gattgttgat ctaatgtgcc acgcaacgtt cacaatgcgc ttgctatcac cagtcagggc 5340
tccaaattac aatttgataa taatggatga ggcccatttc acagatccag ccagtatagc 5400
ggctagaggg tacatatcaa ctcgtgtagg aatgggagag gcagctgcaa tcttcatgac 5460
agcaacaccc cctggaacag ccgatgcctt tcctcagagc aacgctccaa ttcaagatga 5520
agaaagggat atcccggaac gctcatggaa ttcaggcaat gaatggatta ccgactttgt 5580
tgggaagacg gtgtggtttg tccccagcat caaagccgga aatgacatag caaactgctt 5640
gcggaaaaat ggaaaaaagg tcattcaact tagtaggaag acttttgata cagaatatca 5700
aaagaccaaa ctgaatgatt gggacttcgt ggtgacaaca gacatttcag aaatgggagc 5760
caactttaaa gcagatagag tgatcgaccc aagaagatgt ctcaagccag tgattttgac 5820
agatggaccc gagcgggtga tcctggctgg accaatgcca gtcactgcag cgagcgctgc 5880
gcaaaggaga gggagagttg gcaggaaccc acaaaaagaa aatgaccagt acatattcac 5940
gggccagcct ctcaacaatg acgaagacca tgctcactgg acagaagcaa aaatgctgct 6000
ggacaacatc aacacaccag aagggattat accagctctc tttgaaccag aaagggagaa 6060
gtcagccgcc atagacggtg aataccgcct gaagggtgag tccaggaaga ccttcgtgga 6120
actcatgagg aggggtgacc tcccagtttg gctagcccat aaagtagcat cagaagggat 6180
caaatataca gatagaaaat ggtgctttga tggagaacgt aataatcaaa ttttagagga 6240
gaacatggat gtggaaatct ggacaaagga aggagaaaag aaaaaattga gacctaggtg 6300
gcttgatgcc cgcacttatt cagatccctt ggcactcaag gaattcaagg attttgcagc 6360
tggcagaaag tcaatcgccc ttgatcttgt gacagaaata ggaagagtgc cttcacattt 6420
agcccacaga acgagaaacg ccctggacaa tttggtgatg ctgcacacgt cagaacatgg 6480
cggtagggcc tacaggcatg cagtggagga actaccagaa acaatggaaa cactcctact 6540
cttgggactc atgatcttgt taacaggtgg agcaatgctg ttcttgatat caggtaaagg 6600
gattggaaag acttcaatag gactcatctg tgtaattgct tccagtggca tgttatggat 6660
ggccgatgtc ccacttcaat ggatcgcgtc ggctatagtc ctggaatttt tcatgatggt 6720
gttgcttata ccagaaccag aaaagcagag aactccccaa gacaaccaac tcgcatatgt 6780
cgtgataggc atacttacac tggctgcaat agtagcagcc aatgaaatgg gactgttgga 6840
aactacaaag agagatttag gaatgtctaa agaaccaggt gttgtttctc caaccagcta 6900
tttagatgta gacttgcacc cagcatcagc ctggacattg tacgctgtgg ccacaacagt 6960
aataacacca atgttgagac ataccataga gaattccaca gcaaatgtgt ccctggcagc 7020

-continued

```
tatagctaac caggcagtgg tcctgatggg cttagacaaa ggatggccaa tatcgaaaat   7080
ggacttaggc gtaccactac tggcactggg ctgctattca caagtgaacc cactgactct   7140
cacagcggca gtacttttgc tagctacaca ttatgctatt ataggtccag gattgcaggc   7200
aaaagccact cgtgaagctc aaaaaaggac agctgctgga ataatgaaga atccaacggt   7260
ggatgggata atgacaatag acctagatcc tgtaatatac gattcaaaat tcgaaaagca   7320
actaggacag gttatgctcc tagttctgtg tgcagttcaa cttttgttaa tgagaacatc   7380
atgggccttg tgtgaagctc taaccctagc cacaggacca ataacaacac tctgggaagg   7440
atcacctgga aagttttgga acaccacgat agctgtttcc atggctaaca tctttagagg   7500
gagctattta gcaggagctg ggcttgcttt ttctatcatg aaatcagttg gaacaggaaa   7560
gagaggaacg gggtcacaag gcgaaacctt aggagaaaag tggaaaaaga aattaaatca   7620
gttatcccgg aaagagtttg acctttacaa gaaatctgga atcactgaag tggatagaac   7680
agaagccaaa gaagggttga aaagaggaga aataacacgt catgccgtgt ccagaggcag   7740
cgcaaaactt caatggttcg tggagaggaa catggtcatt cccgaaggaa gagtcataga   7800
cttaggctgt ggaagaggag gctggtcata ttactgcgca ggattgaaaa aagttacaga   7860
agtgcgagga tacacaaaag gcggcccagg acacgaagaa ccagtaccta tgtctacata   7920
cggatggaac atagtcaagt taatgagtgg aaaggatgtg ttttatctcc cacctgaaaa   7980
gtgtgacacc ctattgtgtg acattggaga atcttcacca agcccaacag tggaagaaag   8040
cagaactata agagttttga agatggttga accatggcta aaaaataacc agttttgcat   8100
taaagtatta aacccttaca tgccaactgt gattgagcac ctagaaagac tacaaaggaa   8160
acatggagga atgcttgtga gaaatccact ctcacgaaac tccacgcacg aaatgtactg   8220
gatatccaat ggtaccggca acatcgtctc ttcagtcaac atggtatcca gattgctact   8280
gaacagattt acaatgacac acaggagacc caccatagag aaagatgtgg atttgggagc   8340
aggaacccga catgtcaatg cggaaccaga aacacccaat atggacgtca ttggagaaag   8400
aataaaaagg atcaaggagg agcataattc aacatggcac tatgatgatg aaaatcctta   8460
caaaacgtgg gcttaccatg gatcctatga agtcaaagcc acaggctcag cctcctccat   8520
gataaatgga gtcgtgaaac tcctcacaaa accatgggat gtggtgccca tggtgataca   8580
gatggcaatg acagatacaa ctccatttgg gcggcaaaga gttttcaaag agaaagtgga   8640
caccaggaca cccaggccca tgccagggac aagaaaggtt atggagatca cagcggaatg   8700
gctttggaga accctgggaa ggaacaaaag acccagattg tgcacaaggg aagagttcac   8760
aaaaaaggtc agaaccaacg cggctatggg tgccgttttc acagaggaga accaatggga   8820
tagtgcgaga gctgctgttg aggacgagga attctggaaa cttgtggaca gagaacgtga   8880
actccacaaa ttgggcaagt gtggaagctg cgtctacaac atgatgggca agagagagaa   8940
gaaacttgga gagtttggca aagcaaaagg cagtagagct atatggtaca tgtggttggg   9000
agccaggtac cttgagttcg aggcactcgg attcttaaat gaagaccact ggttctcgcg   9060
tgaaaactct tacagtggag tagaaggaga aggactgcac aagctgggat acattttaag   9120
agatatttcc aagatacccg gaggagctat gtatgctgat gacacagctg gttgggacac   9180
aagaataaca gaagatgacc tgcacaatga ggaaaaaatc acacagcaaa tggaccctga   9240
acacagacag ttagcgaacg ccatattcaa gctcacatac caaaacaaag tggtcaaagt   9300
tcaacgacca actccaaaag gcacggtaat ggacatcata tctaggaaag accaaagagg   9360
```

-continued

```
cagtggacag gtggggactt atggtctgaa tacattcacc aacatggaag cccagttagt   9420
cagacagatg gaaggagaag gcgtgttgtc gaaggcagac cttgagaatc ctcatctgct   9480
agagaagaaa atcacacaat ggttggaaac caaaggagtg gagaggttaa aaagaatggc   9540
tatcagtggg gatgattgcg tagtgaaacc gatcgacgac aggtttgcca atgccctgct   9600
tgccctgaac gatatgggaa aggttaggaa ggacatacct caatggcagc catcaaaggg   9660
ttggcatgat tggcaacagg tccctttctg ctcccaccac tttcatgaac tgatcatgaa   9720
agatggaaga aagttggtgg ttccctgcag accccaggac gaactaatag gaagagcgag   9780
aatctctcaa ggagcaggat ggagccttaa agaaactgca tgtctaggga aagcctacgc   9840
tcaaatgtgg agtctcatgt attttcacag aagagatctt agactagcat ccaacgccat   9900
atgttcagca gtaccagtcc attgggtccc tacaagcaga acgacatggt ctattcatgc   9960
tcaccatcag tggatgacta cagaagacat gcttactgtc tggaacaggg tgtggataga  10020
ggacaatcca tggatggaag acaaaactcc agtcacaact tgggaagatg ttccatacct  10080
agggaagaga gaagaccaat ggtgcggatc actcatcggt ctcacttcca gagcaacctg  10140
ggcccagaac atactcacag caatccaaca agtgagaagc cttataggca atgaagagtt  10200
tctggactac atgccttcga tgaagagatt caagaaggag gaggagtcag agggagccat  10260
ttggtaaacg gaggaagtaa aaaagaggca cactgtcagg ccaccttaag ccacagtacg  10320
gaagaagctg tgcagcctgt gagccccgtc caaggacgtt aaaagaagaa gtcaggccca  10380
aaagccacgg tttgagcaaa ccgtgctgcc tgtagctccg tcgtggggac gtaaagcctg  10440
ggaggctgca aactgtggaa gctgtacgca cggtgtagca gactagcggt tagaggagac  10500
ccctcccatg acacaacgca gcagcggggc ccgagcactg agggaagctg tacctccttg  10560
caaaggacta gaggttagag gagacccccc gcaaacaaaa acagcatatt gacgctggga  10620
gagaccagag atcctgctgt ctcctcagca tcattccagg cacagaacgc cagaaaatgg  10680
aatggtgctg ttgaatcaac aggttctcgc gagagctcca gcttttgttc cctttagtga  10740
gggttaattg cgcgcttggc gtaatcatgg tcatagctgt ttcctgtgtg aaattgttat  10800
ccgctcacaa ttccacacaa cataggagcc ggaagcataa agtgtaaagc ctggggtgcc  10860
taatgagtga ggtaactcac attaattgcg ttgcgctcac tgcccgcttt ccagtcggga  10920
aacctgtcgt gccagctgca ttaatgaatc ggccaacgcg cggggagagg cggtttgcgt  10980
attgggcgct cttccgcttc ctcgctcact gactcgctgc gctcggtcgt tcggctgcgg  11040
cgagcggtat cagctcactc aaaggcggta atacggttat ccacagaatc aggggataac  11100
gcaggaaaga acatgtgagc aaaaggccag caaaaggcca ggaaccgtaa aaaggccgcg  11160
ttgctggcgt ttttccatag gctccgcccc cctgacgagc atcacaaaaa tcgacgctca  11220
agtcagaggt ggcgaaaccc gacaggacta taaagatacc aggcgtttcc ccctggaagc  11280
tccctcgtgc gctctcctgt tccgaccctg ccgcttaccg gatacctgtc cgcctttctc  11340
ccttcgggaa gcgtggcgct ttctcatagc tcacgctgta ggtatctcag ttcggtgtag  11400
gtcgttcgct ccaagctggg ctgtgtgcac gaaccccccg ttcagcccga ccgctgcgcc  11460
ttatccggta actatcgtct tgagtccaac ccggtaagac acgacttatc gccactggca  11520
gcagccactg gtaacaggat tagcagagcg aggtatgtag gcggtgctac agagttcttg  11580
aagtggtggc ctaactacgg ctacactaga aggacagtat ttggtatctg cgctctgctg  11640
aagccagtta ccttcggaaa aagagttggt agctcttgat ccggcaaaca aaccaccgct  11700
ggtagcggtg gtttttttgt ttgcaagcag cagattacgc gcagaaaaaa aggatctcaa  11760
```

-continued

```
gaagatcctt tgatcttttc tacggggtct gacgctcagt ggaacgaaaa ctcacgttaa  11820
gggattttgg tcatgagatt atcaaaaagg atcttcacct agatcctttt aaattaaaaa  11880
tgaagtttta aatcaatcta aagtatatat gagtaaactt ggtctgacag ttaccaatgc  11940
ttaatcagtg aggcacctat ctcagcgatc tgtctatttc gttcatccat agttgcctga  12000
ctccccgtcg tgtagataac tacgatacgg gagggcttac catctggccc cagtgctgca  12060
atgataccgc gagacccacg ctcaccggct ccagatttat cagcaataaa ccagccagcc  12120
ggaagggccg agcgcagaag tggtcctgca actttatccg cctccatcca gtctattaat  12180
tgttgccggg aagctagagt aagtagttcg ccagttaata gtttgcgcaa cgttgttgcc  12240
attgctacag gcatcgtggt gtcacgctcg tcgtttggta tggcttcatt cagctccggt  12300
tcccaacgat caaggcgagt tacatgatcc cccatgttgt gcaaaaaagc ggttagctcc  12360
ttcggtcctc cgatcgttgt cagaagtaag ttggccgcag tgttatcact catggttatg  12420
gcagcactgc ataattctct tactgtcatg ccatccgtaa gatgcttttc tgtgactggt  12480
gagtactcaa ccaagtcatt ctgagaatag tgtatgcggc gaccgagttg ctcttgcccg  12540
gcgtcaatac gggataatac cgcgccacat agcagaactt taaaagtgct catcattgga  12600
aaacgttctt cggggcgaaa actctcaagg atcttaccgc tgttgagatc cagttcgatg  12660
taacccactc gtgcacccaa ctgatcttca gcatctttta ctttcaccag cgtttctggg  12720
tgagcaaaaa caggaaggca aaatgccgca aaaaagggaa taagggcgac acggaaatgt  12780
tgaatactca tactcttcct ttttcaatat tattgaagca tttatcaggg ttattgtctc  12840
atgagcggat acatatttga atgtatttag aaaaataaac aaataggggt tccgcgcaca  12900
tttccccgaa aagtgccacc tgaacgaagc atctgtgctt cattttgtag aacaaaaatg  12960
caacgcgaga gcgctaattt ttcaaacaaa gaatctgagc tgcattttta cagaacagaa  13020
atgcaacgcg aaagcgctat tttaccaacg aagaatctgt gcttcatttt tgtaaaacaa  13080
aaatgcaacg cgagagcgct aatttttcaa acaaagaatc tgagctgcat ttttacagaa  13140
cagaaatgca acgcgagagc gctattttac caacaaagaa tctatacttc ttttttgttc  13200
tacaaaaatg catcccgaga gcgctatttt tctaacaaag catcttagat tacttttttt  13260
ctcctttgtg cgctctataa tgcagtctct tgataacttt ttgcactgta ggtccgttaa  13320
ggttagaaga aggctacttt ggtgtctatt ttctcttcca taaaaaaagc ctgactccac  13380
ttcccgcgtt tactgattac tagcgaagct gcgggtgcat tttttcaaga taaaggcatc  13440
cccgattata ttctataccg atgtggattg cgcatacttt gtgaacagaa agtgatagcg  13500
ttgatgattc ttcattggtc agaaaattat gaacggtttc ttctattttg tctctatata  13560
ctacgtatag gaaatgttta cattttcgta ttgttttcga ttcactctat gaatagttct  13620
tactacaatt tttttgtcta aagagtaata ctagagataa acataaaaaa tgtagaggtc  13680
gagtttagat gcaagttcaa ggagcgaaag gtggatgggt aggttatata gggatatagc  13740
acagagatat atagcaaaga gatacttttg agcaatgttt gtggaagcgg tattcgcaat  13800
attttagtag ctcgttacag tccggtgcgt ttttggtttt ttgaaagtgc gtcttcagag  13860
cgcttttggt tttcaaaagc gctctgaagt tcctatactt tctagagaat aggaacttcg  13920
gaataggaac ttcaaagcgt ttccgaaaac gagcgcttcc gaaaatgcaa cgcgagctgc  13980
gcacatacag ctcactgttc acgtcgcacc tatatctgcg tgttgcctgt atatatatat  14040
acatgagaag aacggcatag tgcgtgttta tgcttaaatg cgtacttata tgcgtctatt  14100
```

-continued tatgtaggat gaaaggtagt ctagtacctc ctgtgatatt atcccattcc atgcggggta 14160
tcgtatgctt ccttcagcac taccctttag ctgttctata tgctgccact cctcaattgg 14220
attagtctca tccttcaatg ctatcatttc ctttgatatt ggatcatatt aagaaaccat 14280
tattatcatg acattaacct ataaaaatag gcgtatcacg aggccctttc gtctcgcgcg 14340
tttcggtgat gacggtgaaa acctctgaca catgcagctc ccggagacgg tcacagcttg 14400
tctgtaagcg gatgccggga gcagacaagc ccgtcagggc gcgtcagcgg gtgttggcgg 14460
gtgtcggggc tggcttaact atgcggcatc agagcagatt gtactgagag tgcaccataa 14520
acgacattac tatatatata atataggaag catttaatag acagcatcgt aatatatgtg 14580
tactttgcag ttatgacgcc agatggcagt agtggaagat attctttatt gaaaaatagc 14640
ttgtcacctt acgtacaatc ttgatccgga gcttttcttt ttttgccgat taagaattaa 14700
ttcggtcgaa aaaagaaaag gagagggcca agagggaggg cattggtgac tattgagcac 14760
gtgagtatac gtgattaagc acacaaaggc agcttggagt atgtctgtta ttaatttcac 14820
aggtagttct ggtccattgg tgaaagtttg cggcttgcag agcacagagg ccgcagaatg 14880
tgctctagat tccgatgctg acttgctggg tattatatgt gtgcccaata gaaagagaac 14940
aattgacccg gttattgcaa ggaaaatttc aagtcttgta aaagcatata aaaatagttc 15000
aggcactccg aaatacttgg ttggcgtgtt tcgtaatcaa cctaaggagg atgttttggc 15060
tctggtcaat gattacggca ttgatatcgt ccaactgcat ggagatgagt cgtggcaaga 15120
ataccaagag ttcctcggtt tgccagttat taaaagactc gtatttccaa aagactgcaa 15180
catactactc agtgcagctt cacagaaacc tcattcgttt attcccttgt ttgattcaga 15240
agcaggtggg acaggtgaac ttttggattg gaactcgatt tctgactggg ttggaaggca 15300
agagagcccc gaaagcttac attttatgtt agctggtgga ctgacgccag aaaatgttgg 15360
tgatgcgctt agattaaatg gcgttattgg tgttgatgta agcggaggtg tggagacaaa 15420
tggtgtaaaa gactctaaca aaatagcaaa tttcgtcaaa aatgctaaga aataggttat 15480
tactgagtag tatttattta agtattgttt gtgcacttgc ctatgcggtg tgaaataccg 15540
cacagatgcg taaggagaaa ataccgcatc aggaaattgt aaacgttaat attttgttaa 15600
aattcgcgtt aaatttttgt taaatcagct cattttttaa ccaataggcc gaaatcggca 15660
aaatccctta taaatcaaaa gaatagaccg agatagggtt gagtgttgtt ccagtttgga 15720
acaagagtcc actattaaag aacgtggact ccaacgtcaa agggcgaaaa accgtctatc 15780
agggcgatgg cccactacgt gaaccatcac cctaatcaag ttttttgggg tcgaggtgcc 15840
gtaaagcact aaatcggaac cctaaaggga gcccccgatt tagagcttga cggggaaagc 15900
cggcgaacgt ggcgagaaag gaagggaaga aagcgaaagg agcgggcgct agggcgctgg 15960
caagtgtagc ggtcacgctg cgcgtaacca ccacacccgc cgcgcttaat gcgccgctac 16020
agggcgcgtc gcgccattcg ccattcaggc tgcgcaactg ttgggaaggg cgatcggtgc 16080
gggcctcttc gctattacgc cagctggcga aaggggggatg tgctgcaagg cgattaagtt 16140
gggtaacgcc agggttttcc cagtcacgac gttgtaaaac gacggccagt gagcgcgcgg 16200
ggcgaattgg gtaccgggcc ccccctcgag gtcgactaat acgactcact atag 16254

<210> SEQ ID NO 3
<211> LENGTH: 10708
<212> TYPE: RNA
<213> ORGANISM: Artificial
<220> FEATURE:
<223> OTHER INFORMATION: Full length Arbovax DEN3 clone RNA sequence -continued

<400> SEQUENCE: 3
aguuguuagu cuacguggac cgacaagaac aguuucgacu cggaagcuug cuuaacguag 60
ugcugacagu uuuuuauuag agagcagauc ucugaugaac aaccaacgga aaaagacggg 120
aaaaccgucu aucaauaugc ugaaacgcgu gagaaaccgu gugucaacug gaucacaguu 180
ggcgaagaga uucucaagag gauugcugaa cggccaagga ccaaugaagu ugguuauggc 240
guucauagcu uuccucagau uucuagccau uccaccaaca gcaggagucu uggcuagaug 300
gggaaccuuc aagaagucag gggcuauuaa gguccuaaaa ggcuucaaga aggagauuuc 360
aaacaugcug agcauuauca acaaaaggaa aaagacaucg cucugucuca ugaugauguu 420
accagcaaca cuuaucgauc acuugacuuc acgagaugga gagccgcgca ugauuguggg 480
gaagaaugaa agaggaaaau cccaacuuuu uaagacagcc ucuggaauua acaugugcac 540
acucauagcc auggacuugg gagagaugug ugaugacgcg gucacuuaca aaugcccccca 600
cauuaccgaa guggaaccug aagacauuga cugcuggugc aaccuuacau caacaugggu 660
gacuuaugga acgugcaacc aagcuggaga gcauagacgc gacaaaagau caguggcguu 720
agcuccucau gucggcaugg gacuggacac acgcacccaa accuggaugu cggcugaagg 780
agcuuggaga caagucgaga ggguagagac augggcccuc aggcacccag gguucaccau 840
acuagcccua uuucuugccc auuacauagg cacuuccuug acccagaagg ugguuauuuu 900
uauacuacua augcugguca ccccauccau gacaaugaga ugugugggaa uaggaaacag 960
agauuuugug gaaggucuau caggagcuac gugggguugac guggugcucg agcacggggg 1020
gugugugacu accaugguua agaacaagcc cacgcuggau auagagcuuc agaagaccga 1080
ggccacccaa cuggcgaccc uaaggaagcu augcauugag gggaaaauua ccaacauaac 1140
aacugacuca agauguccua cccaagggga agcgguuuug ccugaggagc aggaccagaa 1200
cuacgugugu aagcauacau acguagacag aggcuggggg aacgguugug gcuuguuugg 1260
caagggaagc uugguaacgu gugcgaaauu ucaaugccug gaaccaaugg agggaaaagu 1320
ggugcaauau gagaaccuca aauacaccgu caucauuaca gugcacacag gagaccaaca 1380
ccagguagga aaugaaaugc agggagucac ggcugagaua acaccucagg caucaaccac 1440
ugaagccauc uugccugaau auggaacccu ugggcuagaa ugcucaccac ggacagguuu 1500
ggauuucaau gaaaugaucu uacuaacaau gaagaacaaa gcauggaugg uacauagaca 1560
augguuuuuu gaccuaccuc uaccauggac aucaggagcu acaacagaaa cgccaacuug 1620
gaacaggaag gagcuucuug ugacauucaa aaacgcacau gcgaaaaaac aagaaguagu 1680
cguccuugga ucgcaagagg gagcaaugca uaccgcacug acaggagcca cagaaaucca 1740
aaacucagga ggcacaagca uuuuugcggg gcacuuaaaa uguagacuua agauggacaa 1800
auuggaacuc aaggggauga gcuaugcaau gugcacgaau accuuugugu ugaagaaaga 1860
agucucagaa acgcagcaug ggacaauacu cauuaagguc gaguacaaag gggaagaugc 1920
accuugcaag auuccuuucu ccacagagga uggacaaggg aaagcucaca auggcagacc 1980
gaucacagcc aacccagugg ugacuaagaa ggaggagccc gucaauauug aggcugagcc 2040
uccuuuuggg gaaagcaaua uaguaauugg aauuggagac aacgccuuga aaaucaacug 2100
guacaagaag ggaagcucua uugggaagau guucgaggcc acugccagag gugcaaggcg 2160
cauggccauc uugggagaca cagcuuggga cuuuggauca gugggguggug uucugaacuc 2220
auuaggcaaa auggugcacc aaauauucgg aagugcuuac acagcccuau ucaguggagu 2280

-continued

```
cucuugggug augaaaauug gaauaggugu ucucuugacu uggauagggu ugaauucaaa   2340
aaacacaucc augucauuuu caugcauugc gauaggaauc auuacacucu aucugggagc   2400
uguggguacaa gcugacaugg ggugugucau aaacuggaaa ggcaaagaac ucaaaugugg   2460
aaguggaauu uucgucacca acgaggucca uaccuggaca gagcaauaca aauuucaagc   2520
agacuccccc aaucgauugg cgacagccau ugcaggcgcc ugggaaaaug gagucugugg   2580
aaucagguca acaaccagaa uggagaaucu auuguggaag caaauagcca augaacugaa   2640
cuacauauua ugggaaaaca acaucaaauu aacgguagug gugggcgaca uaauuggggu   2700
cuuagagcaa gggaaaagaa cacuaacacc acaacccaug gagcuaaaau auucauggaa   2760
aacaugggga aaagcaaaaa uagugacagc ugaaacacaa aauuccucuu ucauaauaga   2820
ugggccaaac acaccggagu guccaagugc cucaagagca uggaaugugu gggaggugga   2880
agauuacggg uuuggagucu ucacaaccaa cauauggcug aaacuccgag agguguacac   2940
ccaauugugc gaccauaggc uaaugucagc agccgucaaa gaugagaggg ccgugcaugc   3000
cgacaugggc uauuggauag aaagccaaaa gaauggaagu uggaagcuag aaaaagcauc   3060
ccucauagag guaaaaaccu gcacuuggcc aaaaucacac acucuuugga guaaugguguu   3120
acuagagagu gacaugauca ucccaaagag ucuaacuggu ccuauuucgc aacacaacca   3180
caggcccggg uaccacaccc aaacggcagg acccuggcac uugggaaaau uggagcugga   3240
cuucaacuau ugugaaggaa caacaguugu caucacagaa aacuguggga caagaggccc   3300
aucauugaga acaacaacag ugucggggaa guugauacac gaaugguguu gccgcucgug   3360
cacacuuccu cccuugcgau acaugggaga agacggcugc ugguauggca uggaaauuag   3420
acccaucaau gagaaagaag agaacauggu aaagucuuua gccucagcag ggaguggaaa   3480
gguggacaac uucacaaugg guguccugug uuuggcaauc cucuucgaag aggugaugag   3540
aggaaaauuu gggaaaaaac acaugauugc aggggguucuc cucacguuug ugcuccuucu   3600
cucagggcaa auaacaugga gagauauggc gcacacacuc auaaugauug gguccaacgc   3660
uucugacagg augggaaugg gcguuaccua ccuagcuuua auugcaacau uuaaaaucca   3720
gccauucuug gcuuugggau ucuuccugag gaaacugaca ucuagagaaa auuuauugcu   3780
gggaguuggg uuggccaugg caacaacguu acaacugcca gaggacauug aacaaauggc   3840
gaauggaauu gcucuggggc ucauggcucu uaaacugaua acacaauuug agacauacca   3900
guuauggacg gcauuagucu cccuaacgug uucaaauaca auuuucacgu ugacuguugc   3960
cuggagaaca gccaccuuga uucuggccgg aguuucgcuu uugccagugu gccagucuuc   4020
gagcaugagg aaaacagauu ggcucccaau ggcuguggca gcuaugggag uuccacccuu   4080
accacuuuuc aucuucagcu ugaaagauac acucaaaagg agaagcuggc cacugaauga   4140
gggggugaug gcuguugggc uugugagcau ucuagcuagc ucucuccuua ggaaugaugu   4200
gcccauggcu ggaccauuag uggccggggg cuugcugaua gcgugcuacg ucauaacugg   4260
cacgucagcg gaccucacug uagaaaaagc agcagaugua acaugggagg aagaggcuga   4320
gcaaacagga guguccccaca auuugaugau cacaguugau gaugauggaa caaugagaau   4380
aaaagaugau gagacugaga acauccuaac agugcucuua aaaacagcau uacuaauagu   4440
aucaggcauc uuuccauauu ccauacccgc cacacuguug gucuggcaua cuuggcaaaa   4500
gcaaacccaa agaucuggcg uucuauggga cguacccagc cccccagaaa cacagaaagc   4560
agaacuggaa gagggggucu auaggaucaa acagcaagga auuuuuggga aaacccaagu   4620
gggggguugga guacagaaag aaggagucuu ccauaccaug uggcacguca caagaggggc   4680
```

-continued agugu ugacg cacaauggga aaagauugga accaaacugg gccagcguga aaaaagaucu 4740
gauuucauac ggaggaggau ggagauugag ugcacaaugg caaaagggag aggaggugca 4800
gguuauugcc guagagcccg ggaagaaccc aaagaacuuu caaaccaugc cgggcauuuu 4860
ucagacaaca acaggggaaa uaggagcaau ugcacuagac uucaagccug gaacuucagg 4920
aucuccuauc auaaacagag agggaaaggu agugggacug uauggcaaug gagugguuac 4980
aaagaauggu ggcuacguca guggaauagc gcaaacaaau gcagaaccag acggaccgac 5040
accggaguug gaagaggaga uguucaaaaa gcgaaaucua accauaaugg aucuucaucc 5100
ugggucagga aagacgcgga aauaucuucc agcuaucguc agagaagcaa ucaagagacg 5160
cuuaagaacu cuaaucuugg caccaacaag ggugguugca gcugagaugg aagaagcauu 5220
gaaagggcuc ccaauaaggu aucaaacaac ugcaacaaaa ucugaacaca caggaaggga 5280
gauuguugau cuaaugugcc acgcaacguu cacaaugcgc uugcuaucac cagucagggc 5340
uccaaauuac aauuugauaa uaauggauga ggcccauuuc acagauccag ccaguauagc 5400
ggcuagaggg uacauaucaa cucguguagg aaugggagag gcagcugcaa ucuucaugac 5460
agcaacaccc ccuggaacag ccgaugccuu uccucagagc aacgcuccaa uucaagauga 5520
agaaagggau aucccggaac gcucauggaa uucaggcaau gaauggauua ccgacuuugu 5580
ugggaagacg gugugguuug uccccagcau caaagccgga aaugacauag caaacugcuu 5640
gcggaaaaau ggaaaaaagg ucauucaacu uaguaggaag acuuuugaua cagaauauca 5700
aaagaccaaa cugaaugauu gggacuucgu ggugacaaca gacauuucag aaaugggagc 5760
caacuuuaaa gcagauagag ugaucgaccc aagaagaugu cucaagccag ugauuuugac 5820
agauggaccc gagcggguga uccuggcugg accaaugcca gucacugcag cgagcgcugc 5880
gcaaaggaga gggagaguug gcaggaaccc acaaaaagaa aaugaccagu acauauucac 5940
gggccagccu cucaacaaug acgaagacca ugcucacugg acagaagcaa aaaugcugcu 6000
ggacaacauc aacacaccag aagggauuau accagcucuc uuugaaccag aaagggagaa 6060
gucagccgcc auagacggug aauaccgccu gaagggugag uccaggaaga ccuucgugga 6120
acucaugagg aggggugacc ucccaguuug gcuagcccau aaaguagcau cagaagggau 6180
caaauauaca gauagaaaau ggugcuuuga uggagaacgu aauaaucaaa uuuuagagga 6240
gaacauggau guggaaaucu ggacaaagga aggagaaaag aaaaaauuga gaccuaggug 6300
gcuugaugcc cgcacuuauu cagaucccuu ggcacucaag gaauucaagg auuuugcagc 6360
uggcagaaag ucaaucgccc uugaucuugu gacagaaaua ggaagagugc cuucacauuu 6420
agcccacaga acgagaaacg cccuggacaa uuuggugaug cugcacacgu cagaacaugg 6480
cgguagggcc uacaggcaug caguggagga acuaccagaa acaauggaaa cacuccuacu 6540
cuugggacuc augaucuugu uaacaggugg agcaaugcug uucuugauau cagguaaagg 6600
gauuggaaag acuucaauag gacucaucug uguaauugcu uccaguggca uguuauggau 6660
ggccgauguc ccacuucaau ggaucgcguc ggcuauaguc cuggaauuuu ucaugauggu 6720
guugcuuaua ccagaaccag aaaagcagag aacuccccaa gacaaccaac ucgcauaugu 6780
cgugauaggc auacuuacac uggcugcaau aguagcagcc aaugaaaugg gacuguugga 6840
aacuacaaag agagauuuag gaaugucuaa agaaccaggu guuguuucuc caaccagcua 6900
uuuagaugua gacuugcacc cagcaucagc cuggacauug uacgcugugg ccacaacagu 6960
aauaacacca auguugagac auaccauaga gaauuccaca gcaaaugugu cccuggcagc 7020

-continued

```
uauagcuaac caggcagugg uccugauggg cuuagacaaa ggauggccaa uaucgaaaau   7080
ggacuuaggc guaccacuac uggcacuggg cugcuauuca caagugaacc cacugacucu   7140
cacagcggca guacuuuugc uagcuacaca uuaugcuauu auagguccag gauugcaggc   7200
aaaagccacu cgugaagcuc aaaaaaggac agcugcugga auaaugaaga auccaacggu   7260
ggaugggaua augacaauag accuagaucc uguaauauac gauucaaaau ucgaaaagca   7320
acuaggacag guuaugcucc uaguucugug ugcaguucaa cuuuuguuaa ugagaacauc   7380
augggccuug ugugaagcuc uaacccuagc cacaggacca auaacaacac ucugggaagg   7440
aucaccugga aaguuuugga acaccacgau agcuguuucc auggcuaaca ucuuuagagg   7500
gagcuauuua gcaggagcug ggcuugcuuu uucuaucaug aaaucaguug gaacaggaaa   7560
gagaggaacg ggggucacaag gcgaaaccuu aggagaaaag uggaaaaaga aauuaaauca   7620
guuaucccgg aaagaguuug accuuuacaa gaaaucugga aucacugaag uggauagaac   7680
agaagccaaa gaaggguuga aaagaggaga aauaacacgu caugccgugu ccagaggcag   7740
cgcaaaacuu caaugguucg uggagaggaa cauggucauu cccgaaggaa gagucauaga   7800
cuuaggcugu ggaagaggag gcuggucaua uuacugcgca ggauugaaaa aaguuacaga   7860
agugcgagga uacacaaaag gcggcccagg acacgaagaa ccaguaccua ugucuacaua   7920
cggauggaac auagucaagu uaaugagugg aaaggaugug uuuuaucucc caccugaaaa   7980
gugugacacc cuauuguggug acauuggaga aucuucacca agcccaacag uggaagaaag   8040
cagaacuaua agaguuuuga agaugguuga accauggcua aaaaauaacc aguuuugcau   8100
uaaaguauua aacccuuaca ugccaacugu gauugagcac cuagaaagac uacaaaggaa   8160
acauggagga augcuuguga gaaauccacu cucacgaaac uccacgcacg aaauguacug   8220
gauauccaau gguaccggca acaucgucuc uucagucaac augguaucca gauugcuacu   8280
gaacagauuu acaaugacac acaggagacc caccauagag aaagaugugg auuugggagc   8340
aggaacccga caugucaaug cggaaccaga aacacccaau auggacguca uuggagaaag   8400
aauaaaaagg aucaaggagg agcauaauuc aacauggcac uaugaugaug aaaauccuua   8460
caaaacgugg gcuuaccaug gauccuauga agucaaagcc acaggcucag ccuccuccau   8520
gauaaaugga gucgugaaac uccucacaaa accaugggau guggugccca uggugauaca   8580
gauggcaaug acagauacaa cuccauuugg gcggcaaaga guuuucaaag agaaagugga   8640
caccaggaca cccaggccca ugccagggac aagaaagguu auggagauca cagcggaaug   8700
gcuuuggaga acccugggaa ggaacaaaag acccagauug ugcacaaggg aagaguucac   8760
aaaaaagguc agaaccaacg cggcuauggg ugccguuuuc acagaggaga accaauggga   8820
uagugcgaga gcugcuguug aggacgagga auucuggaaa cuuguggaca gagaacguga   8880
acuccacaaa uugggcaagu guggaagcug cgucuacaac augaugggca agagagagaa   8940
gaaacuugga gaguuuggca aagcaaaagg caguagagcu auaugguaca ugugguuggg   9000
agccagguac cuugaguucg aggcacucgg auucuuaaau gaagaccacu gguucucgcg   9060
ugaaaacucu uacaguggag uagaaggaga aggacugcac aagcugggau acauuuuaag   9120
agauauuucc aagauacccg gaggagcuau guaugcugau gacacagcug guugggacac   9180
aagaauaaca gaagaugacc ugcacaauga ggaaaaaauc acacagcaaa uggacccuga   9240
acacagacag uuagcgaacg ccauauucaa gcucacauac caaaacaaag uggucaaagu   9300
ucaacgacca acuccaaaag gcacgguaau ggacaucaua ucuaggaaag accaaagagg   9360
caguggacag gugggggacuu auggucugaa uacauucacc aacauggaag cccaguuagu   9420
```

-continued

```
cagacagaug gaaggagaag gcguguuguc gaaggcagac cuugagaauc cucaucugcu   9480
agagaagaaa aucacacaau gguuggaaac caaaggagug gagagguuaa aaagaauggc   9540
uaucaguggg gaugauugcg uagugaaacc gaucgacgac agguuugcca augcccugcu   9600
ugcccugaac gauaugggaa agguuaggaa ggacauaccu caauggcagc caucaaaggg   9660
uuggcaugau uggcaacagg ucccuuucug cucccaccac uuucaugaac ugaucaugaa   9720
agauggaaga aaguuggugg uucccugcag accccaggac gaacuaauag gaagagcgag   9780
aaucucucaa ggagcaggau ggagccuuaa agaaacugca ugucuaggga aagccuacgc   9840
ucaaaugugg agucucaugu auuuucacag aagagaucuu agacuagcau ccaacgccau   9900
auguucagca guaccagucc auugggaccc uacaagcaga acgacauggu cuauucaugc   9960
ucaccaucag uggaugacua cagaagacau gcuuacuguc uggaacaggg uguggauaga  10020
ggacaaucca uggauggaag acaaaacucc agucacaacu ugggaagaug uuccauaccu  10080
agggaagaga gaagaccaau ggugcggauc acucaucggu cucacuucca gagcaaccug  10140
ggcccagaac auacucacag caauccaaca agugagaagc cuuauaggca augaagaguu  10200
ucuggacuac augccuucga ugaagagauu caagaaggag gaggagucag agggagccau  10260
uugguaaacg gaggaaguaa aaaagaggca cacugucagg ccaccuuaag ccacaguacg  10320
gaagaagcug ugcagccugu gagccccguc caaggacguu aaaagaagaa gucaggccca  10380
aaagccacgg uuugagcaaa ccgugcugcc uguagcuccg ucguggggac guaaagccug  10440
ggaggcugca aacuguggaa gcuguacgca cgguguagca gacuagcggu uagaggagac  10500
cccucccaug acacaacgca gcagcggggc ccgagcacug agggaagcug uaccuccuug  10560
caaaggacua gagguuagag gagacccccc gcaaacaaaa acagcauauu gacgcuggga  10620
gagaccagag auccugcugu cuccucagca ucauuccagg cacagaacgc cagaaaaugg  10680
aauggugcug uugaaucaac agguucuc                                     10708
```